United States Patent
Capelli et al.

(10) Patent No.: US 11,813,477 B2
(45) Date of Patent: Nov. 14, 2023

(54) SELECTIVE LASER INDUCED OPTICAL BREAKDOWN IN BIOLOGICAL MEDIUM

(71) Applicant: Soliton, Inc., Houston, TX (US)

(72) Inventors: Christopher C. Capelli, Houston, TX (US); Walter Klemp, Houston, TX (US); David Robertson, Houston, TX (US)

(73) Assignee: Soliton, Inc., Houston, TX (US)

( * ) Notice: Subject to any disclaimer, the term of this patent is extended or adjusted under 35 U.S.C. 154(b) by 341 days.

(21) Appl. No.: 16/486,920

(22) PCT Filed: Feb. 19, 2018

(86) PCT No.: PCT/US2018/018596
§ 371 (c)(1),
(2) Date: Aug. 19, 2019

(87) PCT Pub. No.: WO2018/152460
PCT Pub. Date: Aug. 23, 2018

(65) Prior Publication Data
US 2020/0238100 A1 Jul. 30, 2020

Related U.S. Application Data

(60) Provisional application No. 62/460,867, filed on Feb. 19, 2017.

(51) Int. Cl.
*A61N 5/06* (2006.01)
*A61N 5/00* (2006.01)
(Continued)

(52) U.S. Cl.
CPC ............ *A61N 5/067* (2021.08); *A61B 5/0075* (2013.01); *A61B 5/05* (2013.01); *A61B 5/1032* (2013.01);
(Continued)

(58) Field of Classification Search
CPC .... A61N 5/0616; A61N 5/067; A61B 5/0075; A61B 5/05; A61B 5/1032; A61B 5/441;
(Continued)

(56) References Cited

U.S. PATENT DOCUMENTS 3,364,708 A   1/1968   Padberg
3,475,646 A   10/1969  Chapman
(Continued)

FOREIGN PATENT DOCUMENTS

CN      1245410      2/2000
CN      101028525    9/2007
(Continued)

OTHER PUBLICATIONS

Baumler et al., Q-Switch Laser and Tattoo Pigments: First Results of the Chemical and Photophysical Analysis of 41 Compounds, Lasers in Surgery and medicine 26:13-21 (2000), pp. 13-21.
(Continued)

*Primary Examiner* — Pamela M. Bays
(74) *Attorney, Agent, or Firm* — Mintz, Levin, Cohn, Ferris, Glovsky and Popeo, P.C.

(57) ABSTRACT

Apparatuses and methods for selectively providing laser induced optical breakdown (LIOB) of absorptive targets in biological media. For example, LIOB may be used as part of tissue therapy, such as cosmetic therapy associated with tattoo removal. In some implementation, a system for selectively providing LIOB includes a field generator configured to generate a field and to apply the field through a portion of a biological medium. The system also includes a light source configured to deliver laser light to the portion of the biological medium during application of the field. Application of the field to the biological medium induces movement of free electrons within the portion of the biological medium
(Continued)

which may reduce or slow the formation of vacuoles in the biological medium responsive to the laser light.

6 Claims, 22 Drawing Sheets

(51) Int. Cl.
*A61B 5/05* (2021.01)
*A61B 5/103* (2006.01)
*A61N 5/067* (2006.01)
*A61B 5/00* (2006.01)
*A61B 18/00* (2006.01)

(52) U.S. Cl.
CPC ............ *A61B 5/441* (2013.01); *A61N 5/0616* (2013.01); *A61B 2018/00452* (2013.01); *A61B 2018/00577* (2013.01)

(58) Field of Classification Search
CPC .......... A61B 2018/00452; A61B 2018/00577; A61B 18/203; A61F 9/00825
See application file for complete search history.

(56) References Cited

U.S. PATENT DOCUMENTS

| | | |
|---|---|---|
| 3,604,641 A | 9/1971 | Wilson et al. |
| 3,613,069 A | 10/1971 | Cary |
| 3,735,764 A | 5/1973 | Balev |
| 3,769,963 A | 11/1973 | Goldman et al. |
| 3,942,531 A | 3/1976 | Hoff |
| 4,005,314 A | 1/1977 | Zinn |
| 4,311,147 A | 1/1982 | Hausler |
| 4,556,051 A | 12/1985 | Maurer |
| 4,715,376 A | 12/1987 | Nowacki et al. |
| 4,858,597 A | 8/1989 | Kurtze et al. |
| 4,896,673 A | 1/1990 | Rose et al. |
| 4,905,671 A | 3/1990 | Senge et al. |
| 4,928,671 A | 5/1990 | Reichenberger et al. |
| 4,955,143 A | 9/1990 | Hagelauer |
| 4,962,752 A | 10/1990 | Reichenberger et al. |
| 4,979,501 A | 12/1990 | Valchanov et al. |
| 5,009,232 A | 4/1991 | Hassler et al. |
| 5,015,929 A | 5/1991 | Cathignol et al. |
| 5,030,196 A * | 7/1991 | Inoue ............... A61N 2/12 600/14 |
| 5,071,422 A | 12/1991 | Watson et al. |
| 5,146,912 A | 9/1992 | Eizenhoefer |
| 5,149,406 A * | 9/1992 | Mullen ............... H01S 3/305 204/157.44 |
| 5,150,713 A | 9/1992 | Okazaki |
| 5,193,527 A | 3/1993 | Schafer |
| 5,195,508 A | 3/1993 | Muller et al. |
| 5,204,820 A | 4/1993 | Strobel et al. |
| 5,231,976 A | 8/1993 | Wiksell |
| 5,240,005 A | 8/1993 | Viebach |
| 5,245,988 A | 9/1993 | Einars et al. |
| 5,259,368 A | 11/1993 | Wiksell |
| 5,284,143 A | 2/1994 | Rattner |
| 5,304,170 A | 4/1994 | Green |
| 5,304,207 A | 4/1994 | Stromer |
| 5,327,890 A | 7/1994 | Matura et al. |
| 5,360,447 A | 11/1994 | Koop |
| 5,374,236 A | 12/1994 | Hassler |
| 5,393,296 A | 2/1995 | Rattner |
| 5,409,446 A | 4/1995 | Rattner |
| 5,419,327 A | 5/1995 | Rohwedder et al. |
| 5,423,803 A | 6/1995 | Tankovich et al. |
| 5,435,304 A | 7/1995 | Oppelt et al. |
| 5,458,652 A | 10/1995 | Uebelacker |
| 5,509,200 A | 4/1996 | Frankeny et al. |
| 5,529,572 A | 6/1996 | Spector |
| 5,595,178 A | 1/1997 | Voss et al. |
| 5,618,275 A | 4/1997 | Bock |
| 5,658,239 A | 8/1997 | Delmenico |
| 5,675,495 A | 10/1997 | Biermann et al. |
| 5,676,159 A | 10/1997 | Navis |
| 5,709,676 A | 1/1998 | Alt |
| 5,722,411 A | 3/1998 | Suzuki |
| 5,737,462 A * | 4/1998 | Whitehouse ......... G02B 6/4296 250/281 |
| 5,790,305 A | 8/1998 | Marcellin-Dibon et al. |
| 5,827,204 A | 10/1998 | Grandia et al. |
| 6,013,122 A | 1/2000 | Klitzman et al. |
| 6,036,661 A | 3/2000 | Schwarze et al. |
| 6,039,694 A | 3/2000 | Larson et al. |
| 6,058,932 A | 5/2000 | Hughes |
| 6,080,119 A | 6/2000 | Schwarze et al. |
| 6,096,029 A | 8/2000 | O'Donnell, Jr. |
| 6,113,559 A | 9/2000 | Klopotek |
| 6,113,560 A | 9/2000 | Simnacher |
| 6,123,679 A | 9/2000 | Lafaut et al. |
| 6,176,839 B1 | 1/2001 | Deluis et al. |
| 6,186,963 B1 | 2/2001 | Schwarze et al. |
| 6,210,329 B1 | 4/2001 | Christmas et al. |
| 6,217,531 B1 | 4/2001 | Reitmajer |
| 6,309,355 B1 | 10/2001 | Cain et al. |
| 6,325,769 B1 | 12/2001 | Klopotek |
| 6,350,245 B1 | 2/2002 | Cimino |
| 6,368,929 B1 | 4/2002 | Hill et al. |
| 6,390,995 B1 | 5/2002 | Ogden et al. |
| 6,450,979 B1 | 9/2002 | Miwa et al. |
| 6,454,713 B1 | 9/2002 | Ishibashi et al. |
| 6,487,447 B1 | 11/2002 | Weimann et al. |
| 6,491,685 B2 | 12/2002 | Visuri |
| 6,500,141 B1 | 12/2002 | Irion et al. |
| 6,515,842 B1 | 2/2003 | Hayworth et al. |
| 6,519,376 B2 | 2/2003 | Biagi et al. |
| 6,551,308 B1 | 4/2003 | Muller et al. |
| 6,666,834 B2 | 12/2003 | Restle et al. |
| 6,755,821 B1 | 6/2004 | Fry |
| 6,800,122 B2 | 10/2004 | Anderson et al. |
| 6,905,467 B2 | 6/2005 | Bradley |
| 6,942,663 B2 | 9/2005 | Vargas et al. |
| 6,948,843 B2 | 9/2005 | Laugharn et al. |
| 6,972,116 B2 | 12/2005 | Brill et al. |
| 7,189,209 B1 | 3/2007 | Ogden et al. |
| 7,250,047 B2 | 7/2007 | Anderson et al. |
| 7,311,678 B2 | 12/2007 | Spector |
| 7,364,554 B2 | 4/2008 | Bolze et al. |
| 7,405,510 B2 | 6/2008 | Kaminski et al. |
| 7,470,240 B2 | 12/2008 | Schultheiss et al. |
| 7,507,213 B2 | 3/2009 | Schultheiss et al. |
| 7,588,547 B2 | 9/2009 | Deem et al. |
| 7,867,178 B2 | 1/2011 | Simnacher |
| 7,985,189 B1 | 7/2011 | Ogden et al. |
| 7,988,631 B2 | 8/2011 | Bohris |
| 8,057,408 B2 | 11/2011 | Cain et al. |
| 8,088,073 B2 | 1/2012 | Simnacher et al. |
| 8,092,401 B2 | 1/2012 | Schultheiss |
| 8,102,734 B2 | 1/2012 | Sliwa et al. |
| 8,235,899 B2 | 8/2012 | Hashiba |
| 8,257,282 B2 | 9/2012 | Uebelacker et al. |
| 8,298,162 B2 | 10/2012 | Del Giglio |
| 8,323,220 B2 | 12/2012 | Babaev |
| 8,343,420 B2 | 1/2013 | Cioanta et al. |
| 8,357,095 B2 | 1/2013 | Anderson et al. |
| 8,672,721 B2 | 3/2014 | Camilli |
| 8,684,970 B1 | 4/2014 | Koyfman |
| 2002/0009015 A1 | 1/2002 | Laugharn et al. |
| 2002/0193831 A1 | 12/2002 | Smith |
| 2003/0167964 A1 | 9/2003 | Anderson et al. |
| 2003/0233045 A1 | 12/2003 | Vaezy |
| 2004/0006288 A1 | 1/2004 | Spector et al. |
| 2004/0181219 A1 | 9/2004 | Goble et al. |
| 2005/0015023 A1 | 1/2005 | Ein-Gal |
| 2005/0049543 A1 | 3/2005 | Anderson et al. |
| 2005/0107852 A1 | 5/2005 | Levernier et al. |
| 2005/0150830 A1 | 7/2005 | Laugharn et al. |
| 2006/0036168 A1 | 2/2006 | Liang et al. |
| 2006/0064082 A1 | 3/2006 | Bonutti |
| 2006/0158956 A1 | 7/2006 | Laugharn et al. |
| 2006/0173388 A1 | 8/2006 | Ginter et al. |

(56) References Cited

U.S. PATENT DOCUMENTS

| | | |
|---|---|---|
| 2006/0184071 A1 | 8/2006 | Klopotek |
| 2006/0200116 A1 | 9/2006 | Ferren et al. |
| 2006/0211958 A1 | 9/2006 | Rosenberg et al. |
| 2006/0259102 A1* | 11/2006 | Slatkine ............... A61M 5/422 607/88 |
| 2007/0016112 A1 | 1/2007 | Schultheiss et al. |
| 2007/0038060 A1 | 2/2007 | Cerwin et al. |
| 2007/0049829 A1 | 3/2007 | Kaminski et al. |
| 2007/0055157 A1 | 3/2007 | Bohris |
| 2007/0055180 A1 | 3/2007 | Deem et al. |
| 2007/0065420 A1 | 3/2007 | Johnson |
| 2007/0135755 A1 | 6/2007 | Bernabei et al. |
| 2007/0198068 A1 | 8/2007 | Chan et al. |
| 2007/0219760 A1 | 9/2007 | Yang et al. |
| 2007/0239072 A1 | 10/2007 | Schultheiss et al. |
| 2007/0239082 A1 | 10/2007 | Schultheiss et al. |
| 2007/0239084 A1 | 10/2007 | Voss |
| 2007/0249939 A1 | 10/2007 | Gerbi et al. |
| 2008/0009774 A1 | 1/2008 | Capelli et al. |
| 2008/0009885 A1 | 1/2008 | Del Giglio |
| 2008/0021447 A1 | 1/2008 | Davison et al. |
| 2008/0071198 A1 | 3/2008 | Ogden et al. |
| 2008/0107744 A1 | 5/2008 | Chu |
| 2008/0132810 A1 | 6/2008 | Scoseria et al. |
| 2008/0146971 A1 | 6/2008 | Uebelacker et al. |
| 2008/0154157 A1 | 6/2008 | Altshuler et al. |
| 2008/0183200 A1 | 7/2008 | Babaev |
| 2008/0194967 A1 | 8/2008 | Sliwa et al. |
| 2008/0195003 A1 | 8/2008 | Sliwa et al. |
| 2008/0262483 A1 | 10/2008 | Capelli et al. |
| 2008/0269163 A1 | 10/2008 | Sostaric |
| 2008/0269608 A1 | 10/2008 | Anderson et al. |
| 2008/0319356 A1 | 12/2008 | Cain et al. |
| 2009/0018472 A1 | 1/2009 | Soltani et al. |
| 2009/0062644 A1 | 3/2009 | McMorrow et al. |
| 2009/0088824 A1* | 4/2009 | Baird ................... A61N 5/0617 607/90 |
| 2009/0275832 A1 | 11/2009 | Gelbart et al. |
| 2010/0049098 A1 | 2/2010 | Shalgi et al. |
| 2010/0076349 A1 | 3/2010 | Babaev |
| 2010/0082019 A1 | 4/2010 | Neev |
| 2010/0087899 A1 | 4/2010 | Erez et al. |
| 2010/0168575 A1 | 7/2010 | Hashiba |
| 2010/0204617 A1 | 8/2010 | Ben-Ezra |
| 2010/0208467 A1 | 8/2010 | Dross |
| 2010/0249768 A1 | 9/2010 | Avramenko et al. |
| 2010/0274161 A1 | 10/2010 | Azhari et al. |
| 2010/0280420 A1 | 11/2010 | Barthe et al. |
| 2010/0331741 A9 | 12/2010 | Cioanta et al. |
| 2011/0034832 A1 | 2/2011 | Cioanta et al. |
| 2011/0087157 A1 | 4/2011 | Cioanta et al. |
| 2012/0157892 A1 | 6/2012 | Reitmajer et al. |
| 2012/0167174 A1 | 6/2012 | Saxena et al. |
| 2012/0253240 A1 | 10/2012 | Uebelacker et al. |
| 2012/0253416 A1 | 10/2012 | Erez et al. |
| 2012/0310232 A1 | 12/2012 | Erez |
| 2012/0323147 A1 | 12/2012 | Scheirer |
| 2012/0330288 A1 | 12/2012 | Clementi et al. |
| 2013/0018287 A1 | 1/2013 | Capelli |
| 2013/0046179 A1 | 2/2013 | Humayun |
| 2013/0046207 A1 | 2/2013 | Capelli |
| 2013/0345600 A1 | 12/2013 | Katragadda et al. |
| 2014/0005576 A1 | 1/2014 | Adams et al. |
| 2014/0094718 A1 | 4/2014 | Feldman |
| 2014/0228820 A1 | 8/2014 | Blaskowski et al. |
| 2014/0243715 A1 | 8/2014 | Cioanta et al. |
| 2014/0243847 A1 | 8/2014 | Hakala et al. |
| 2014/0257144 A1 | 9/2014 | Capelli et al. |
| 2014/0276693 A1 | 9/2014 | Altshuler et al. |
| 2014/0276722 A1 | 9/2014 | Parihar et al. |
| 2014/0277219 A1 | 9/2014 | Nanda |
| 2014/0378740 A1 | 12/2014 | Wagner et al. |
| 2015/0105702 A1 | 4/2015 | Wagner et al. |
| 2015/0126913 A1 | 5/2015 | Jurna et al. |
| 2015/0217111 A1 | 8/2015 | Stevenson et al. |
| 2016/0016013 A1 | 1/2016 | Capelli et al. |
| 2016/0067139 A1 | 3/2016 | Katragadda et al. |
| 2016/0166837 A1 | 6/2016 | Strommer et al. |
| 2016/0262778 A1 | 9/2016 | Du |
| 2016/0271419 A1* | 9/2016 | Varghese ............. A61B 18/042 |
| 2018/0116905 A1 | 5/2018 | Capelli et al. |
| 2018/0221688 A1 | 8/2018 | Cioanta et al. |

FOREIGN PATENT DOCUMENTS

| | | |
|---|---|---|
| CN | 101146574 | 3/2008 |
| CN | 101155614 | 4/2008 |
| CN | 100530868 | 8/2009 |
| CN | 101610736 | 12/2009 |
| CN | 102057422 | 5/2011 |
| CN | 102247661 | 11/2011 |
| CN | 105209117 | 12/2015 |
| CN | 105246419 | 1/2016 |
| DE | 3150430 | 7/1983 |
| DE | 3710371 | 10/1988 |
| DE | 60008898 | 1/2005 |
| DE | 102007046902 | 4/2009 |
| EP | 0008647 | 3/1980 |
| EP | 0243650 | 11/1987 |
| EP | 0322473 | 7/1989 |
| EP | 0326620 | 8/1989 |
| EP | 2964326 | 1/2016 |
| EP | 3626307 | 3/2020 |
| FR | 2605874 | 5/1988 |
| GB | 2303552 | 2/1997 |
| JP | 53-111689 | 9/1978 |
| JP | S61-293447 | 12/1986 |
| JP | S 61-293447 | 12/1986 |
| JP | 62-192150 | 8/1987 |
| JP | S 63-023775 | 2/1988 |
| JP | S63-183050 | 7/1988 |
| JP | S 63-183050 | 7/1988 |
| JP | 6-7365 | 1/1994 |
| JP | H06-505648 | 6/1994 |
| JP | H 06-505648 | 6/1994 |
| JP | H0673654 | 10/1994 |
| JP | 8-140984 | 6/1996 |
| JP | H 08140984 | 6/1996 |
| JP | 8-194079 | 7/1996 |
| JP | 1996-222472 | 8/1996 |
| JP | H0-8224253 | 9/1996 |
| JP | 9-103434 | 4/1997 |
| JP | H09103434 | 4/1997 |
| JP | H 10192289 | 7/1998 |
| JP | H 10328192 | 12/1998 |
| JP | 2003-500126 | 1/2003 |
| JP | 2004526507 | 9/2004 |
| JP | 2005514142 | 5/2005 |
| JP | 2007-000218 | 1/2007 |
| JP | 2009-506870 | 2/2009 |
| JP | 2009-518126 | 4/2009 |
| JP | 2009-527262 | 7/2009 |
| JP | 2009-543614 | 12/2009 |
| JP | 2012-516170 | 7/2012 |
| JP | 2013-537559 | 10/2013 |
| JP | 2014-507990 | 4/2014 |
| JP | 2014-525782 | 10/2014 |
| JP | 2016/523602 | 8/2016 |
| JP | 2017-500078 | 1/2017 |
| JP | 61-73644 | 8/2017 |
| KR | 101886863 | 8/2018 |
| RU | 2121812 | 11/1998 |
| RU | 2151559 | 6/2000 |
| TW | 200604017 | 2/2006 |
| TW | I 292341 | 1/2008 |
| TW | I 350249 | 10/2011 |
| WO | WO 91/10227 | 7/1991 |
| WO | WO 2000/071207 | 11/2000 |
| WO | WO 2002/030256 | 4/2002 |
| WO | WO 2004/080147 | 9/2004 |
| WO | WO 2007/067563 | 6/2007 |
| WO | WO 2007/088546 | 8/2007 |
| WO | WO 2007/146988 | 12/2007 |
| WO | WO 2008/052198 | 5/2008 |

(56) References Cited

FOREIGN PATENT DOCUMENTS

| WO | WO 2008/074005 | 6/2008 |
|---|---|---|
| WO | WO 2008/137942 | 11/2008 |
| WO | WO 2010/086301 | 8/2010 |
| WO | WO 2010/122517 | 10/2010 |
| WO | WO 2011/077466 | 6/2011 |
| WO | WO 2011/091020 | 7/2011 |
| WO | WO 2012/107830 | 8/2012 |
| WO | WO 2013/012724 | 1/2013 |
| WO | WO 2014/138582 | 9/2014 |
| WO | WO 2014/191263 | 12/2014 |
| WO | WO 2015/176001 | 11/2015 |
| WO | WO 2017/165595 | 9/2017 |
| WO | WO 2018/136514 | 7/2018 |

OTHER PUBLICATIONS

Bickle, Abdominal X Rays Made Easy: Calcification, Student BMJ vol. 10, Aug. 2002, 272-274.
Burov, et al., "Nonlinear Ultrasound: Breakdown of Microscopic Biological Structures and Nonthermal Impact on Malignant Tumor," *Doklady Biochemistry and Biophysics*, 383(3), pp. 101-104. (2002).
Chen et al., "The disappearance of ultrasound contrast bubbles: Observations of bubble dissolution and Cavitation nucleation", Ultrasound in Med. & Biol., vol. 28, No. 6, pp. 793-803, 2002.
Delius, et al., "Biological Effects of Shock Waves: Kidney Haemorrhage by Shock Waves in Dogs—Administration Rate Dependence," *Ultrasound Med Biol.*, 14(8), 689-694, 1988.
Eisenmenger, W. et al., "The First Clinical Results of Wide-Focus and Low-Pressure ESWL" Ultrasound in Med. & Biol., vol. 28, No. 6, pp. 769-774, 2002.
Eisenmenger, Wolfgang, "The Mechanisms of Stone Fragmentation in ESWL", Ultrasound in Med. & Biol., vol. 27, No. 5, pp. 683-693, 2001.
Falco, "Single-Point Nonlinearity Indicators for the Propagation of High Amplitude Acoustic Signals," Ph.D. Thesis. Graduate Program in Acoustics, The Pennsylvania State University, University Park, PA, May 2007.
Fernando, "A Nonlinear Computational Method for the Propagation of ShockWaves in Aero-Engine Inlets Towards a New Model for Buzz-Saw Noise Prediction," 15$^{th}$ AIAA/CEAS Aerocoustics Conference (30$^{th}$ Aerocoustics Conference) May 11-13, 2009, 1-18.
Gillitzer, et al., "Low-Frequency Extracorporeal Shock Wave Lithotripsy Improves Renal Pelvic Stone Disintegration An a Pig Model," *BJU Int*, 176, 1284-1288, 2009.
Ho et al., "Laser-Tattoo Removal—A Study of the Mechanism and the Optimal Treatment Strategy via Computer Simulations", Lasers in Surgery and medicine 30:389-391 (2002).
International Preliminary Report on Patentability Issued in Corresponding PCT Patent Application No. PCT/US2018/018596, dated Jun. 23, 2019.
International Search Report and Written Opinion Issued in Corresponding PCT Patent Application No. PCT/US2018/018596, dated May 17, 2018.
Kuhn et al., "Impact of extracorporeal shock waves on the human skin with cellulite: A case study of an unique instance", *Clinical Interventions of Aging*, 3(1):201-210, 2008.
Kuperman-Beade et al., "Laser Removal of Tattoos", Am J Clin Dermatol 2001: 2(1):21-25.
Kuzmin et al., "Ultrasonic Cavitational Chemical Technologies", XI Session of the Russian Acoustical Society, Moscow, Nov. 19-23, 2001.
Liu, et al., "Optimized Design of LED Freeform Lens for Uniform Circular Illumination," *Journal of Zhejiang University—Science C*, Computer & Electron, 13(12), 929-936, 2012.
Madbouly, et al., "Slow Versus Fast Shock Wave Lithotripsy Rate for Urolithiasis: A Prospective Randomized Study," *The Journal of Urology*, 173, 127-130, 2005.

Nana, et al., "Application of the Multiple Low-Energy Q-Switched Laser for the Treatment of Tattoos in 21 Cases," China Aesthetic Medicine, 4(21), 621-622, 2012. (English Abstract).
Ng et al., "Therapeutic Ultrasound: Its Application in Drug Delivery", Medicinal Research Reviews, vol. 22, No. 2, 204-223, 2002.
Ogden et al., Principles of Shook Wave Therapy, Clinical Orthopaedics and Related Research, No. 387, pp. 8-17.
Reichenberger, "Electromagnetic Acoustic Source for Extracorporeal Generation of Shock Waves in Lithotripsy," Siemens Forsch, 1986, 187-194.
Ross et al., "Comparison of Responses of Tattoos to Picosecond and Nanosecond Q-Switched Neodymium: YAG Lasers" ARCH Dermatol/ vol. 134, Feb. 1998, pp. 167-171.
Sheth and Pandya, "Melsama: A comprehensive update (Part I)", *Journal of the American Academy of Dermatology*, 65:689-697, 2011.
Sheth and Pandya, "Melsama: A comprehensive update (Part II)", *Journal of the American Academy of Dermatology*, 65:699-714, 2011.
Solis et al., "Experimental Nonsurgical Tattoo Removal in a Guinea Pig Model with Topical Imiquimod and Tretinoin", Dermatol Surg. 2002, 28:83-87.
Timko et al., "In Vitro Quantitative Chemical Analysis of Tattoo Pigments", ARCH Dermatol/vol. 137, Feb. 2001, pp. 143-147.
Varma, S., "Tattoo Ink Darkening of a yellow Tattoo after Q-Switched Laser Treatment", 2002 Blackwell Science Ltd., Clinical and Experimental Dermatology, 27, 461-463.
Vogel, et al., "ShockWave Emission and Cavitation Bubble Generation by Picosecond and Nanosecond Optical Breakdown in Water," J. Acoust. Soc. Am., 100 (1) Jul. 1996.
Wolfrum et al., "Shock wave induced interaction of microbubbles and boundaries", Physics of Fluids, vol. 15, No. 10, Oct. 2003, pp. 2916-2922.
Office Action Issued in Chinese Patent Application No. 201910058064, dated Feb. 8, 2021.
Boxman, et al., "Handbook of Vacuum Arc Science and Technology: Fundamentals and Applications," Park Ridge, New Jersey: Noyes Publications, pp. 316-319, 1995.
Extended European Search Report Issued in Corresponding European Patent Application No. 20153807.1, dated Jun. 9, 2020.
International Preliminary Report on Patentability Issued in Corresponding PCT Application No. PCT/US2017/042122, dated Jan. 22, 2019.
International Search Report and Written Opinion Issued in Corresponding PCT Application No. PCT/US2017/042122, dated Jan. 9, 2018.
International Search Report and Written Opinion Issued in Corresponding PCT Application No. PCT/US14/21746, dated Sep. 12, 2014.
Office Action Issued in Corresponding Japanese Patent Application No. 2019-012062, dated Jun. 16, 2020.
Partial Supplementary Search Report Issued in Corresponding European Patent Application No. EP18754679.1, dated Jul. 29, 2020.
Schmitz, et al., "Treatment of Chronic Plantar Fasciopathy with Extracorporeal Shock Waves (Review)," *Journal of Orthopaedic Surgery and Research*, 8(1); 31, 2013.
Ushakov, et al., "Impulse Breakdown of Liquids," New York, New York: Springer.
International Search Report and Written Opinion issued in Corresponding PCT Application No. PCT/US2020/026425, dated Sep. 2, 2020.
Office Action and Search Report issued in Corresponding Chinese Application No. 201780056472.0, dated Jan. 19, 2022 (English Translation provided).
Office Action issued in Australian Patent Application No. 2021201670, dated Jun. 20, 2022.
Office Action issued in U.S. Appl. No. 16/478,611, dated Jun. 30, 2022.
Troilius, "Effective Treatment of traumatic Tattoos with a Q-switched Nd:YAG laser," Lasers Surg. Med., 22:103-108, 1998.
Carlberg, "Upgrading from Stepper to Servo," Yaskawa America Inc., pp. 1-7, 2011.

(56) References Cited

OTHER PUBLICATIONS

Manousakas et al., "Development of a system of automatic gap-adjusted electrodes for shock wave generators," Review of Scientific Instruments, 75(11):4811-4819, 2004.
Office Action issued in U.S. Appl. No. 16/478,611, dated Oct. 31, 2022.
English translation of Office Action issued in Japanese Patent Application No. 2021-184610, dated Nov. 18, 2022.
Office Action issued in Australian Patent Application No. 2018221251, dated Nov. 10, 2022.
Official Action issued in Japanese Patent Application No. 2019-544631, dated Sep. 16, 2022.
English translation of Office Action issued in Korean Patent Application No. 10-2019-7005043 dated Sep. 28, 2022.
Office Action issued in U.S. Appl. No. 16/087,976 dated Oct. 13, 2022.
Notice of Allowance issued in U.S. Appl. No. 17/648,790, dated Feb. 28, 2023.
Office Communication issued in Japanese Patent Application No. 2018-550349, dated Mar. 7, 2023.
Office Communication issued in U.S. Appl. No. 16/904,125, dated Mar. 23, 2023.
Office Communication issued in U.S. Appl. No. 17/096,932, dated Mar. 28, 2023.
Office Communication issued in U.S. Appl. No. 16/319,509, dated Apr. 10, 2023.

* cited by examiner

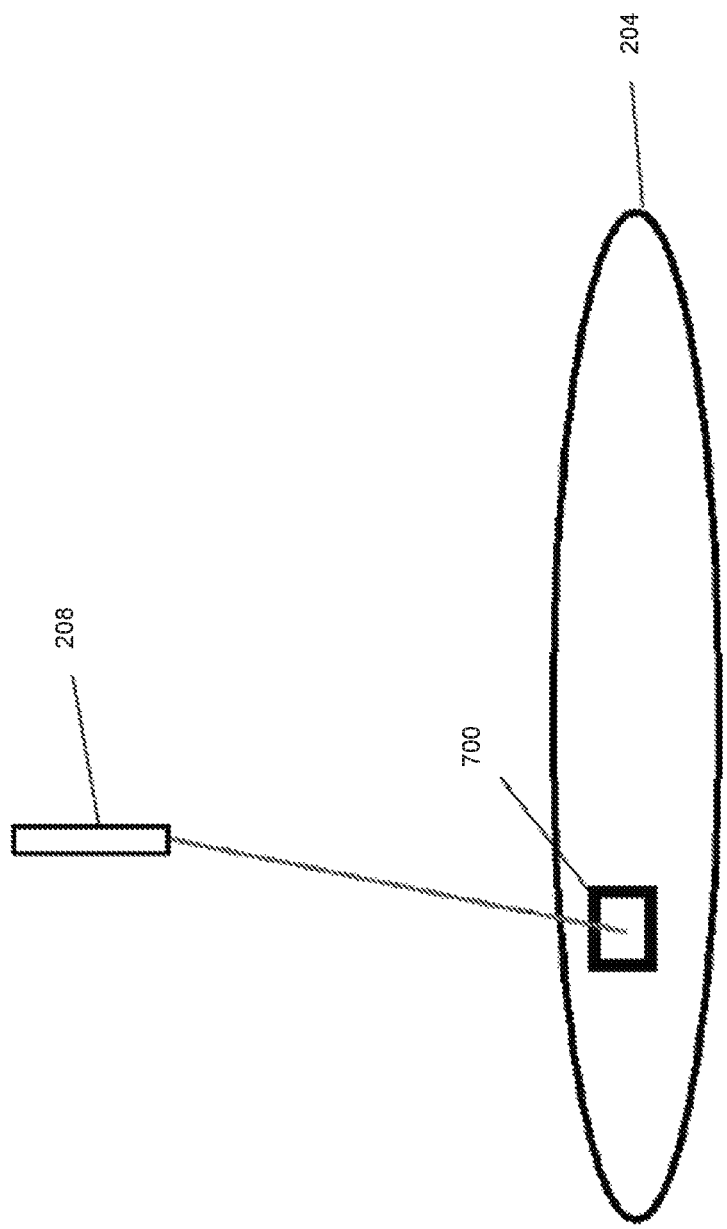

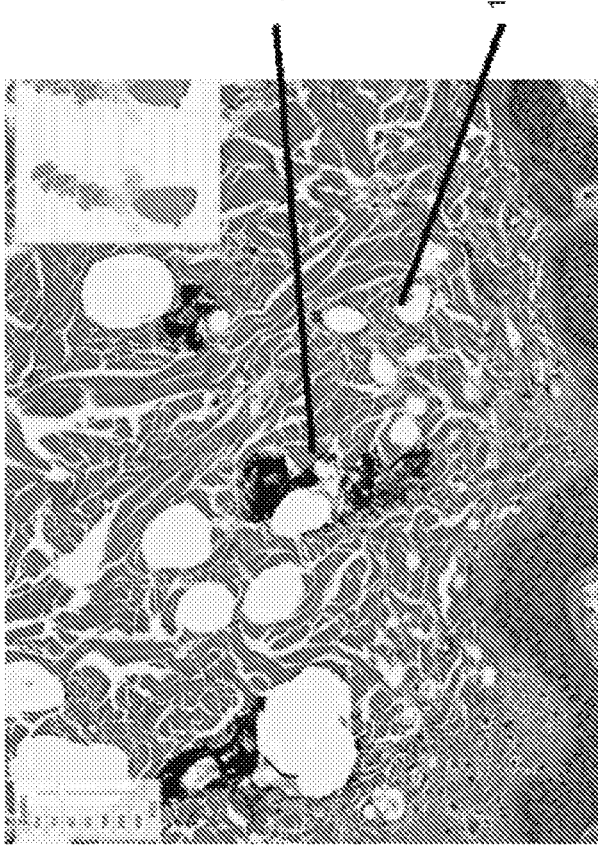
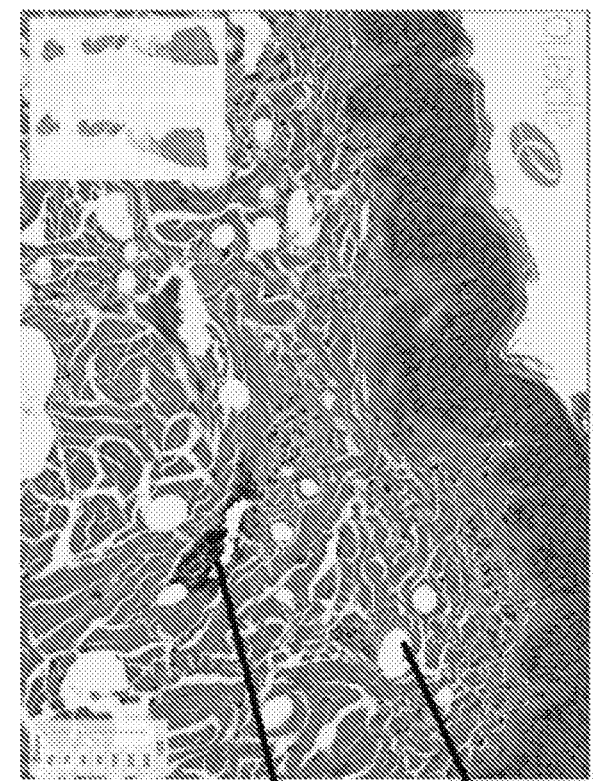
FIG. 13A
FIG. 13B

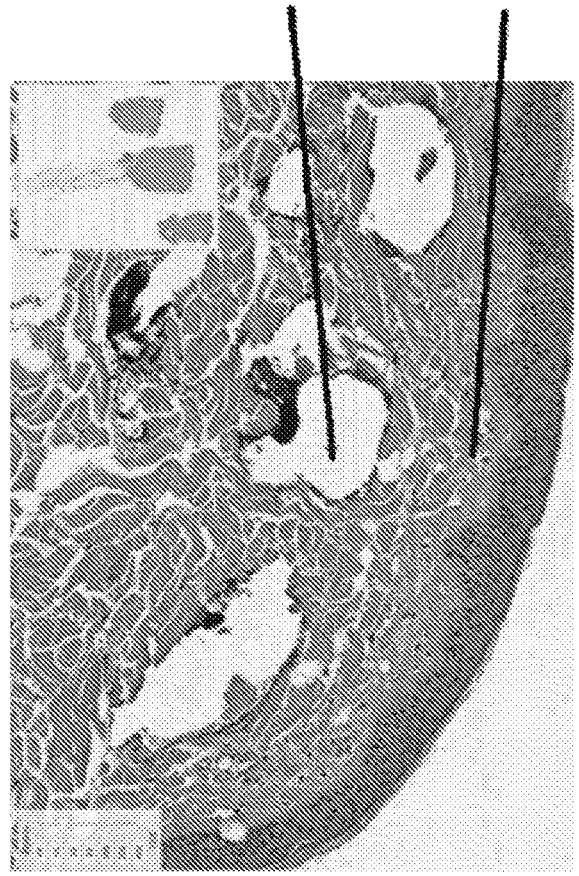
FIG. 15A
FIG. 15B

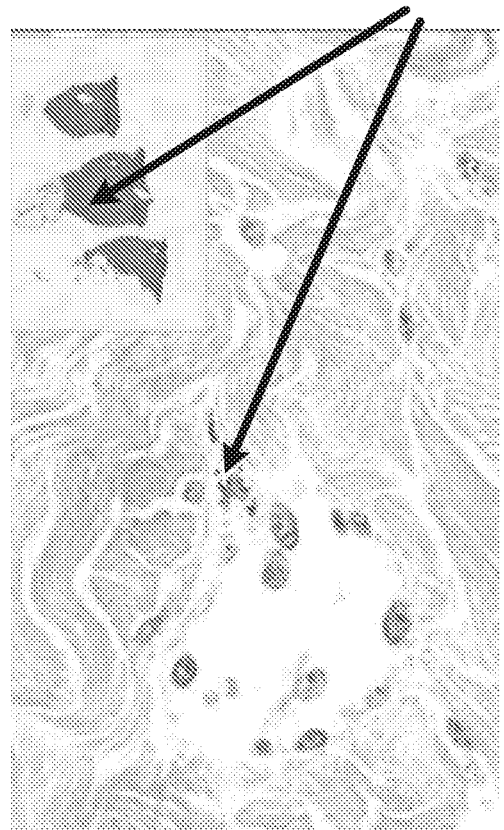
FIG. 16B
FIG. 16A

Dermal Injury: Laser Vs EFE Laser

Percent Tattoo Fading at 8 Weeks

SELECTIVE LASER INDUCED OPTICAL BREAKDOWN IN BIOLOGICAL MEDIUM

CROSS-REFERENCE TO RELATED APPLICATIONS

This application is a national phase application under 35 U.S.C. § 371 of International Application No. PCT/US2018/018596 filed Feb. 19, 2018, which claims benefit of U.S. Provisional Patent Application No. 62/460,867 filed Feb. 19, 2017, all of which are incorporated herein by reference in their entirety.

TECHNICAL FIELD

The present disclosure relates generally to therapeutic uses of a laser. More particularly, but not by way of limitation, the present disclosure relates to systems, apparatuses, and methods of using a field, such as an electric field, a magnetic field, or both, to selectively produce laser induced optical breakdown (LIOB) in a biological medium.

BACKGROUND

High-powered pulsed lasers have been used for certain therapies for a number of years. In the medical context, "laser" is generally used to refer to a coherent light source used to treat or remove tissue. Examples of pulsed laser therapies include laser vein removal, laser hair removal, and laser tattoo removal. Each of these therapies typically involves targeting a laser at a biological medium and pulsing the laser (e.g., a "laser beam" or "laser light") into the biological medium where the beam or light is absorbed by an absorptive target, such as a vein, hair follicle, or tattoo pigment particle, in the biological medium. For example, using the appropriate wavelength of light, the pulsed laser can lead to ablation of tattoo ink particles in the dermis from laser induced optical breakdown (LIOB), which leads to tattoo fading. In other laser-based therapies, such as skin tightening, the biological medium itself is the absorptive target. When the absorptive target is in a non-transparent medium such as tissue, ablating pigment particles is less efficient as compared to ablating pigment particles in a transparent medium, such as water.

Laser induced optical breakdown (LIOB) is the catastrophic evolution of damage inflicted in a medium by a beam of high laser fluence, which results in electron avalanche (e.g., a build of free carries in a relatively short time) and plasma formation. This effect is based on the acceleration of free electrons to high energies that cause collisions with other atoms or molecules and lead to secondary free carriers. To illustrate, the LIOB process for pigment particle ablation related to tattoo removal begins with a small number of free electrons that naturally occur in the biological medium, or from those that are generated by laser-induced (multi-photon) ionization or through a thermal initiation pathway (i.e., thermionic emission). Electron avalanche can develop if these electrons are able to gain enough energy from the laser beam that they are able to ionize atoms, resulting in increased collisions and further stripping of ions and electrons. Repetition of the process can lead to a rapid accumulation of free electrons. As a result, "cascade ionization" or "electron avalanche" occurs that results in the formation of a plasma plume adjacent to the pigment particle surface.

When the level of ionization and plasma formation becomes appreciable, the incoming laser energy can be readily absorbed by the free electrons in the plasma plume via free-free transitions in the field of ions. This absorption causes intense heating of the plasma and consequentially a rapid expansion of the plasma plume in the form of a shock wave. Because of this, a visible photon release appears and the intense heat causes formation of one or more vacuoles (e.g., steam cavitation bubbles) adjacent to the pigment particle. The plasma plume can form in the range of a nanosecond and the vacuoles (e.g., dermal vacuoles) form shortly thereafter. If the vacuoles are large enough, the vacuoles can result in laser attenuation and scattering (laser shielding), each of which can contribute to a loss of laser effectiveness during a laser-based therapy.

U.S. Pat. No. 5,149,406 describes suppressing LIOB events by quenching the free electrons present in transparent, non-conductive gaseous medium, such as an $SF_6$ environment. However, unlike the transparent, non-conductive gaseous medium, a biological medium is conductive obtain a high enough voltage to provide quenching of the free electrons would require an electric current level that would be dangerous to the patient. Additionally, quenching the free electrons in a biological medium has been considered non-feasible because it has been thought that no electric field could be generated within a conductive medium—i.e., with no electric field, there would be no electromotive force on free electrons.

Referring to FIGS. 1A-1C, illustrative examples of biological mediums subjected to a conventional pulsed-laser therapy treatment are shown. Each of FIGS. 1A and 1B depict a histological image of a tattooed site post laser treatment. Specifically, FIG. 1A shows a biopsy of dermis tissue taken within one minute of laser treatment and FIG. 1B shows a biopsy of dermis tissue taken immediately post-treatment of a treatment with fluence of 9.0 J/cm². FIG. 1C depicts an example of "whitening" from nanosecond laser treatment of a tattoo.

Referring to FIGS. 1A and 1B, the histological images show examples of vacuoles (e.g., dermal vacuoles) that can form in a biological medium as a result of a LIOB caused by a pulsed laser. For example, when a pulsed laser is used to affect an absorptive target in a biological medium, such as a tattoo pigment agglomeration 104 in dermis tissue, LIOB events can result in formation of at least two different types of vacuoles that can be characterized by their location within the dermis. The different types of vacuoles can include "particle vacuoles" 100 and "remote vacuoles" 102.

A laser pulse into a tattoo pigment agglomeration 104 (e.g., an absorptive target) can produce an LIOB event at the surface of the pigment agglomeration 104. The LIOB event leads to ablation damage to the absorptive target and to the formation of a steam vacuole—i.e. a "particle vacuole" 100—located immediately adjacent to the absorptive target on the side that is closest to the pulsed laser source. The particle vacuoles 100 are typically large, asymmetrically shaped, and usually appear adjacent to pigment particles. In addition to particle vacuoles 100, additional vacuoles—referred to as "remote vacuoles" 102—may form in biological media (e.g., dermis, adipose, muscle, etc.) away from or remote to pigment particles such that remote vacuoles 102 do not appear to be directly associated with the pigment particle surfaces. Remote vacuoles 102 are typically smaller and can appear more spherical than particle vacuoles 100.

It is noted that, while laser-based therapies in biological media without absorptive targets (e.g., pigment particles) typically do not generate remote vacuoles 102, when an absorptive target (e.g., pigment particles) is present in the biological medium, remote vacuoles 102 can be generated.

To illustrate, a LIOB event at the pigment particle surface can act as a source of free electrons within the medium (e.g., dermis, adipose, muscle, etc.). Remote vacuoles 102 can form when pulsed laser light photons interact with the free electrons resulting in an avalanche cascade of free electrons and formation of a plasma bubble that leads to the production of steam and, thus, remote vacuole 102.

Referring to FIG. 1C, an example of a black tattoo that has been pulse laser treated is shown. The ablation of the pigment particles results from LIOB events at the pigment particle surface which leads to generation of epidermal and dermal vacuoles (i.e., "whitening") in the skin.

Both particle vacuoles 100 and remote vacuoles 102 cause laser shielding of the absorptive target, resulting in laser attenuation and scattering which leads to decreased laser effectiveness against the absorptive target. Consequently, as a result of the vacuoles (e.g., remote vacuoles 120), only a percentage of initial laser energy reaches its intended target and attempts to immediately repeat pulsed laser treatments of the whitened tattoo are ineffective. The absorption time of vacuoles into surrounding tissue can take anywhere from minutes to hours. Additionally, LIOB events that occur in biological media are highly destructive to surrounding cellular structures. For example, the release of heat and the shockwave damage to cells in and around a treatment cite of the biological medium can lead to necrotizing vasculitis, which in turn leads to significant collagen damage and epidermal scabbing 24-48 hours post-laser treatment. In an attempt to counteract this damage, the laser fluence during a treatment session can be reduced or limited, which reduces an overall efficacy of the treatment. Repeated pulsed laser treatments of the tattooed skin is ineffective without significant rest times between laser treatment sessions to allow the vacuole to be absorbed by the surrounding tissue and/or to allow recovery from the skin damage (e.g., epidermal scabbing). Additionally, as a result of vacuoles that form during a laser-based therapy (e.g., a tattoo removal session), practitioners have difficulty in achieving the maximum desired therapeutic effect from and/or providing repeated pulsed laser treatments to a specific site in the biological medium during a single treatment session. Therefore, completion of laser therapy in a single treatment session has generally not been feasible as a result of the presence of these laser shielding vacuoles.

SUMMARY

The present disclosure includes examples of methods, apparatuses, and systems for providing selective laser induced optical breakdown (LIOB) in a biological medium, such as a conductive biological medium. For example, LIOB may be used as part of tissue therapy, such as cosmetic therapy associated with tattoo removal, in which the LIOB is directed toward an absorptive target (e.g., tattoo pigment particles) within a biological medium. During tissue therapy, a field, such as an electrostatic field (e.g., high voltage with minimal current), is applied to or generated in a biological medium, thereby inhibiting LIOB of the biological medium itself while allowing for selective LIOB at the absorptive target. For example, the field may inhibit formation of remote vacuoles while permitting particle vacuole formation associated with a pigment agglomeration. To illustrate, when a tattoo site is treated with a pulsed laser, the ablation of the pigment particles cause conductive conditions of the dermis to become unstable such that, when the field (e.g., the electrostatic field) is applied to the dermis, internal electromotive forces act to move free electrons. The free electrons can be moved (e.g., dispersed) from the laser pulse path, thereby reducing a concentration of the free elections and thus inhibiting remote vacuole formation while permitting particle vacuole formation.

The present methods, apparatuses, and systems can thereby reduce and/or limit remote vacuole formation as compared to conventional techniques in which a pulse laser is applied without application of a field (e.g., an electrostatic field). Accordingly, laser effectiveness against an absorptive target is greater when the field is applied as compared to conventional techniques when no field is applied. Because application of the field reduces and/or limits remote vacuole formation, laser treatments over the same treatment area may be performed in quick succession and effectively to whitened tattoo areas, and/or without negatively impacting surrounding cellular structures. Additionally, laser fluence during a treatment session does not need to be reduced or limited, which permits a greater desired therapeutic effect to be realized during a single treatment session as compared to conventional techniques. By having a treatment session that is more effective as compared to conventional techniques, a patient has to undergo a fewer total number of treatments and thereby experiences less discomfort and a short treatment duration.

In some embodiments, the selective laser-induced optical breakdown in a conductive biological medium targets an absorptive target within the conductive biological medium. In some embodiments, an electric field is generated in a biological medium thereby inhibiting laser induced optical breakdown of the biological medium itself while allowing for selective laser induced optical breakdown at the absorptive target. A voltage source with high voltage and low current can provide an electrostatic field sufficient to be used in a conductive biological medium to selectively provide LIOB.

If dielectric (or insulator) films are placed between the positive and negative plates of a voltage source with a conductive medium (e.g., salt water) between these insulator films, there will be no electric field standing in the conductive medium. The polarization of the electric charges within the dielectric material creates an internal electric field that reduces the overall field within the dielectric film itself. Therefore, no electric field exists in the conductive medium between the dielectric covered plates. However, if a conductive medium comprises a complex mixture of dielectric and polar molecules—such as a biological medium like skin—and is further perturbed by a high energy source such as a laser thereby generating free electrons, ions, and plasmas, the conductive medium electrically becomes part of the dielectric insulators over the voltage plates. In this scenario, electric fields can be induced causing sufficient electromotive force to move free electrons within the biological media.

Under normal, stable conditions, biological media are typically conductive. When placed in an electrostatic field, a conductive medium should not produce any internal electric field. As a result, with no electric field, no electromotive force exists to move free electrons within the biological medium. However, when treated with a pulsed laser, the conductive biological medium briefly is able to produce internal electromotive forces that act to move free electrons within the biological medium. This results from the biological medium's normal, stable conditions becoming unstable when treated with a laser. Perturbations in the cells within the biological medium from the laser pulse result in localized disturbances in ionic conductivity. As a result, the conductive medium acts like a dielectric material for a brief period of time. This in turn allows an electrostatic field to briefly induce an electric field within the biological medium causing the free electrons to be effected by an electromotive force within the biological medium.

In some implementations, a system for selectively providing LIOB includes a field generator configured to generate a field and to apply the field through a portion of a biological medium. The field generator may include a plurality of electrodes, a magnetic coil, an electret, or a combination thereof. The system also includes a light source, such as a pulse laser (e.g., a QS-laser), configured to deliver laser light to the portion of the biological medium during application of the field. Application of the field to the biological medium may induce movement of free electrons within the portion of the biological medium which may reduce or slow the formation of vacuoles in the biological medium responsive to the laser light.

In one aspect, the light source and the field generator may be integrated into a single device. In some implementations, the wherein the field generator is configured to be removably coupled to the light source. In another aspect, the light source pulses the laser beam between at least two insulated electrodes that are part of an auxiliary device (e.g., the field generator). During each laser pulse, high voltage (1 kV to 5 kV) is placed across the electrodes to create an electrostatic field at the treatment site. Due to this field, free electrons emitted into the dermis during the particle LIOB event may be quickly swept away from the laser beam path. This removal of free electrons aids in impeding the initiation of dermal LIOBs without affecting the laser ablation of the pigment particle. As a result, remote vacuoles and the accompanying dermal damage are significantly reduced.

In some implementations, the system also includes a head device. The head device may be configured to contact a surface of the biological medium. In some implementations, the head device includes the field generator and/or is physically coupled to the light source. Additionally, or alternatively, the head device may include a vacuum head configured to apply suction to a portion of the biological medium, a window through which light can reach the biological medium, or both.

Some embodiments of the present apparatuses (e.g., for providing cosmetic tissue therapy) comprise: a field generator configured to generate a field and to apply the field through a portion of a biological medium; and a light source configured to deliver laser light to the portion of the biological medium during application of the field. In some such embodiments, the field generator is configured to apply the field to the biological medium to induce movement of free electrons within the portion of the biological medium, and delivery of the laser light to the portion of the biological medium provides optical breakdown of tissue pigment particles.

In some embodiments, the field generator comprises a plurality of electrodes configured to provide the field across the plurality of electrodes, and wherein the field comprises an electrical field. In some such embodiments, the plurality of electrodes comprises a first electrode and a second electrode, the first electrode includes an electrically conductive surface configured to contact the biological medium, and the second electrode is configured to be electrically insulated with respect to the biological medium. Additionally, or alternatively, the field generator comprises a magnetic coil, and the field comprises a magnetic field. Additionally, or alternatively, the field generator comprises an electret, and the field comprises an electrical field. In a particular embodiment, the electret is transparent.

In some embodiments, the light source comprises a pulsed laser. In some such embodiments, the light source is configured to deliver the laser beam with a pulse rate of at least 1 Hz and a fluence of 0.5 J/cm$^2$ to 20 J/cm$^2$. In other such embodiments, the light source is configured to deliver the laser beam with a pulse rate of at least 1 Hz and a fluence of 3.5 J/cm$^2$ to 9 J/cm$^2$.

In some embodiments, the present apparatuses further comprise a power source configured to be electrically coupled to the field generator, the light source, or both. The power source may be configured to provide a voltage to the field generator within a range of 500 to 500,000 volts or −500 to −500,000 volts. In other implementations, the power source may be configured to provide a voltage to the filed generator within a range of 1,200 to 5,000 volts or −1,200 to −5,000 volts. Additionally, or alternatively, the present apparatuses further comprise a probe configured to be coupled to the power source, wherein the probe includes the field generator and the light source. In some embodiments, wherein the field generator is configured to be removably coupled to the light source.

In some embodiments, the present apparatuses further comprise a head device configured to contact a surface of the biological medium. In some such embodiments, the head device includes the field generator, the head device is physically coupled to the light source, the head device includes a window through which light can reach the portion of the biological medium, or a combination thereof. In embodiments where the head device includes the window, the window may include an electret. Additionally, or alternatively, the head device comprises a vacuum head configured to be connected to a vacuum source and to apply suction to the portion of the biological medium, the vacuum head configured to permit light to reach the portion of the biological medium during application of the suction.

Some embodiments of the present apparatuses (e.g., for providing tissue therapy) comprise: a voltage source; and a plurality of electrodes configured to provide an electrical field across the plurality of electrodes; where the voltage source is electrically connected to the electrodes; where a first one of the electrodes comprises an electrically conductive surface configured to contact the biological medium, and a second one of the electrodes is configured to not conduct current to the biological medium; and where the plurality of electrodes are configured to apply the electric field to a portion of a biological medium such that free electrons are affected in the portion of the biological medium. In some embodiments, the plurality of electrodes are configured to apply the electric field to a portion of a biological medium such that free electrons are moved in the portion of the biological medium. In some embodiments, the electric field is a negative electric field. In some embodiments, the second one of the electrodes is spaced from the biological medium or includes an electrically insulating material configured to impede electrical conduction between the second electrode and the biological medium.

Some embodiments of the present apparatuses further comprise: a vacuum head configured to be connected to a vacuum source; where the plurality of electrodes are contained within the vacuum head; where the vacuum head is configured to apply suction to the portion of the biological medium; and where the vacuum head is configured to permit light to reach the portion of the biological medium when suction is applied. In some embodiments, the vacuum head comprises a window through which light can reach the portion of the biological medium. In some embodiments, the vacuum source that the vacuum head is configured to be connected to is a central vacuum system. In some embodiments, the vacuum head is disposable.

Some embodiments of the present apparatuses further comprise: a therapeutic laser system configured to deliver a laser beam through the window to the portion of the biological medium; where the laser beam has an axis; and where the electrical field applied to the portion of the biological medium, when suction is applied to the portion of the biological medium by the vacuum head, is perpendicular to the axis of the laser beam. In some embodiments, the therapeutic laser system includes a pulsed laser. In some embodiments, the therapeutic laser system is configured to deliver laser light to the portion of the biological medium; the plurality of electrodes extend from the therapeutic laser system; and the plurality of electrodes are configured to provide the electrical field when the therapeutic laser system is positioned to deliver the laser light to the portion of the biological medium.

Some embodiments of the present apparatuses further comprise: a magnetic coil; where the voltage source is further configured to provide power to the magnetic coil; and where the magnetic coil, when so powered, is configured to induce a magnetic field in the portion of the biological medium.

Some embodiments of the present systems utilize an electret, instead of or in addition to the electrodes and voltage source, to provide an electric field. Some such embodiments comprise: an electret configured to provide an electrical field; where the electret is configured to apply the electric field to a portion of a biological medium such that free electrons are affected in the portion of the biological medium. In some embodiments, the electret is configured to apply the electric field to a portion of a biological medium such that free electrons are moved in the portion of the biological medium. To illustrate, the free electrons may be removed from the portion of the biological medium, as an illustrative, non-limiting example. In some embodiments, the electret is transparent. In some embodiments, the electret is configured to be spaced from the biological medium or includes an electrically insulating material configured to impede electrical conduction between the electret and the biological medium. In some embodiments, the electret is configured to contact the biological material. Some embodiments further comprise: a therapeutic laser system configured to deliver a laser beam to the portion of the biological medium; where the electret is configured to permit transmission of the laser beam through the electret; and where the therapeutic laser system is further configured to deliver the laser beam to the portion of the biological medium by transmitting the laser beam through the electret.

Some embodiments of the present methods comprise: actuating an electric field generation system to apply an electric field through a portion of a biological medium; and delivering laser light to the portion of the biological medium. In some embodiments, the electric field generation system includes an electret. In some embodiments, the electrical field applied across the plurality of electrodes is a negative electrical field. In some embodiments, the electrical field applied across the plurality of electrodes is a positive electrical field.

Some embodiments of the present methods comprise: actuating a field generator to generate a field; applying the field through a portion of a biological medium; and delivering laser light from a light source to the portion of the biological medium during application of the field. In some such embodiments, applying the field includes moving free electrons within the portion of the biological medium. Additionally, or alternatively, the present methods may further comprise, prior to actuating the field generator, positioning the field generator adjacent to the biological medium at a first location; and, prior to delivering the laser light, positioning the light source with respect to the portion of the biological medium to deliver the laser light to the portion.

In some embodiments, the present methods further comprise providing optical breakdown of tissue pigment particles. Additionally, or alternatively, the present methods may further comprise placing a vacuum head in contact with a surface of the biological medium; and applying a negative pressure to the vacuum head to stabilize at least the portion of the biological medium, wherein the at least the portion of the biological medium is stabilized during delivery of the laser light to the portion.

In some embodiments, the present methods further comprise, after delivering the laser light: positioning the field generator adjacent to the biological medium at a second location; positioning the light source with respect to another portion of the biological medium; actuating the field generator to generate another field; applying the other field through the other portion of the biological medium; and delivering additional laser light from the light source to the other portion of the biological medium during application of the other field.

Some embodiments of the present methods comprise: placing a vacuum head containing a plurality of electrodes in contact with the surface of a biological medium, where the plurality of electrodes are spaced apart from each other, a first one of the electrodes comprises an electrically conductive surface contacting the biological medium, and a second one of the electrodes configured to not conduct current to the biological medium; applying a negative pressure to the vacuum head to stabilize the biological medium; applying an electrical potential across the plurality of electrodes creating an electric field in the biological medium; and delivering laser light to the biological medium at a point between the plurality of electrodes. In some embodiments, the second one of the electrodes is spaced from the biological medium or is separated from the biological medium by an electrically insulating material.

Some embodiments of the present methods comprise: placing a plurality of electrodes relative to a surface of a biological medium such that the electrodes are spaced apart from each other, an electrically conductive surface of a first one of the electrodes contacts the biological medium, and a second one of the electrodes is configured to not conduct current to the biological medium; applying an electrical potential across the plurality of electrodes to create an electric field in the biological medium; and delivering laser light to the biological medium at a point between the plurality of electrodes. In some embodiments, the second one of the electrodes is spaced from the biological medium or is separated from the biological medium by an electrically insulating material. In some embodiments, the electrical potential applied across the plurality of electrodes is a negative electrical potential. In some embodiments, electrical potential applied across the plurality of electrodes is a positive electrical potential. In some embodiments, the laser beam delivered in the space between the plurality of electrodes is a pulsed laser beam.

As used herein, various terminology is for the purpose of describing particular implementations only and is not intended to be limiting of implementations. For example, as used herein, an ordinal term (e.g., "first," "second," "third," etc.) used to modify an element, such as a structure, a component, an operation, etc., does not by itself indicate any priority or order of the element with respect to another element, but rather merely distinguishes the element from another element having a same name (but for use of the ordinal term). The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent. The phrase "and/or" means and or. To illustrate, A, B, and/or C includes: A alone, B alone, C alone, a combination of A and B, a combination of A and C, a combination of B and C, or a combination of A, B, and C. In other words, "and/or" operates as an inclusive or. In the disclosed embodiments, the term "adjacent" is generally defined as located immediately adjacent to the absorptive target on the side that is closest to the pulsed laser.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system or apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Any of the present systems, apparatuses, and methods described herein can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb. Additionally, it will be understood that the term "wherein" may be used interchangeably with "where."

Further, a device, system, or structure (e.g., a component of an apparatus) that is configured in a certain way is configured in at least that way, but it can also be configured in other ways than those specifically described. The feature or features of one embodiment may be applied to other embodiments, even though not described or illustrated, unless expressly prohibited by this disclosure or the nature of the embodiments.

Some details associated with the embodiments are described above, and others are described below. Not all embodiments of the present disclosure include one or more of the described aspects. Other implementations, advantages, aspects, and features of the present disclosure will become apparent after review of the entire application, including the following sections: Brief Description of the Drawings, Detailed Description, and the Claims.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the embodiment depicted in the figures.

FIG. 7 depicts a block diagram of an example of an apparatus that includes an electret and that is configured to selectively provide LIOB to an absorptive target in a biological medium.

FIGS. 13A and 13B depict histological images of "Laser Only" treated tattooed dermis.

FIGS. 15A and 15B depict histological images of "Laser+EF(−)" treated tattooed dermis.

FIGS. 16A and 16B depict histological images of tattoo sites two days after being treated with "Laser+EF(−)" treatment.

DETAILED DESCRIPTION

Figure 1A:
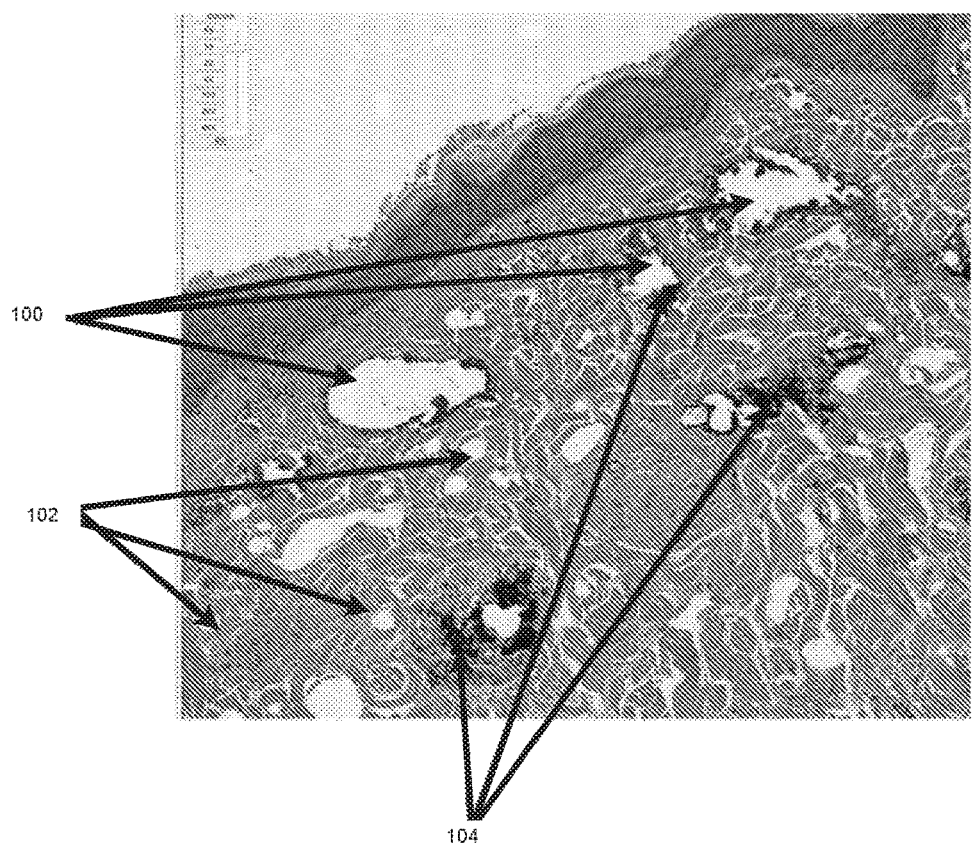
FIGS. 1A and 1B depict histological images of laser treated tattooed dermis demonstrating particle vacuoles and remote vacuoles.
Figure 1B:
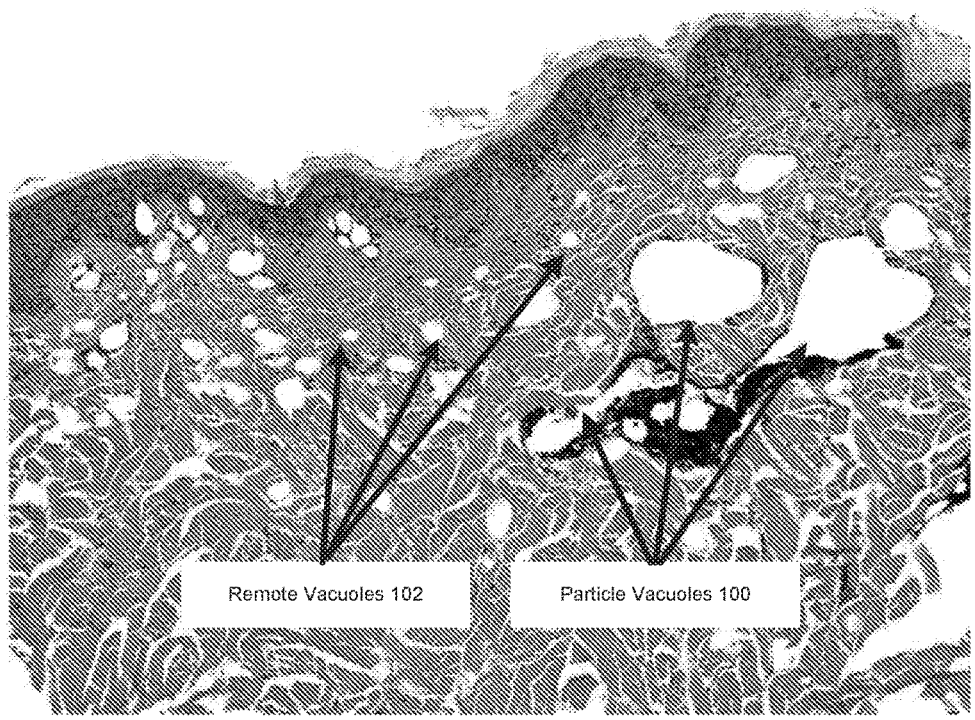
Figure 1C:
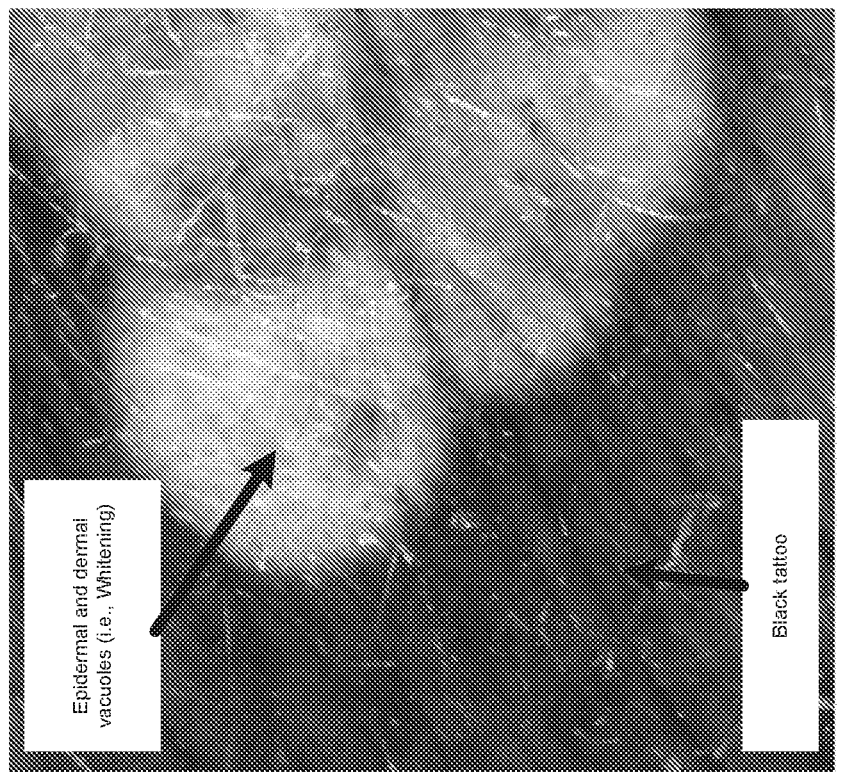
FIG. 1C is a photograph of whitening from epidermal and dermal vacuole formation from nanosecond laser treatment of a tattoo.
Figure 2:
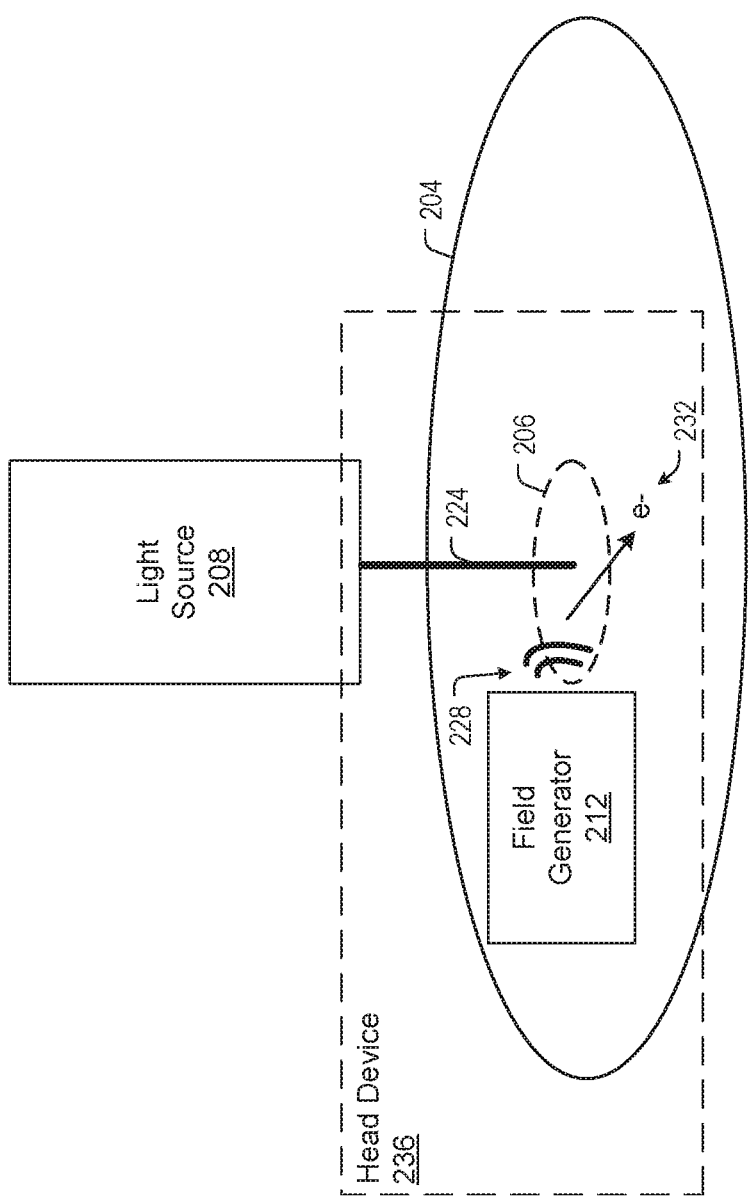
FIG. 2 depicts a block diagram of an example of a system for treating a portion of a biological medium.

Referring to FIG. 2, an example of a system for selectively providing laser induced optical breakdown (LIOB) is depicted. For example, the system may be configured to provide selective LIOB in a conductive biological medium, such as a target 206 (e.g., an absorptive target) in a biological medium 204 (e.g., skin and/or tissue). In some implementations, a portion (e.g., target 206) of biological medium 204 includes a tattoo pigment agglomeration. For example, LIOB may be used as part of tissue therapy, such as cosmetic therapy associated with tattoo removal.

System include a light source 208 and a field generator 212. Light source 208 is configured to generate therapeutic light 224 and deliver at least a portion of light 224 (e.g., therapeutic light) to biological medium 204. To illustrate, as an illustrative, non-limiting example, light source 208 includes a therapeutic laser system configured to deliver a laser light to target 206 of biological medium 204. Light source 208 may include a pulsed laser, such as a Q-switched (QS) laser. For example, in some implementations, light source 208 can include a short-pulsed, high fluence laser, such as a nanosecond 1064 nm Q-switched Nd:YAG laser or a picosecond-laser). To illustrate, light source 208 may be configured to deliver light 224 (e.g., a laser beam) with at least a pulse rate of 1 Hertz (Hz) and a fluence of 3.5 J/cm$^2$ to 9 J/cm$^2$, as an illustrative, non-limiting example. In other implementations, the pulse rate may be greater than or less than 1 Hz. For example, the pulse rate may be within a range of 1-10 Hz or may be greater than 10 Hz. Additionally, or alternatively, the fluence may be less than 3.5 J/cm$^2$ or greater than 9 J/cm$^2$. In a particular implementation, the fluence may be within a range of 0.5 J/cm$^2$ to 20 J/cm$^2$.

The field generator 212 is configured to generate a field 228, such as an electrostatic field, that is applied to biological medium 204. In some implementations, field 228 includes an electrical field, a magnetic field, or both. Field 228 applied to biological medium 204 may cause free electrons, such as representative free electron 232, within target 206 to be affected such that the free electrons (e.g., 232) vacate or are otherwise diverted away from target 206. To illustrate, application of field 228 may repel free electrons (e.g., 232) away from a portion (including a tattoo pigment agglomeration) of biological medium 204 that is targeted to receive light 224. Field generator 212 may be configured to configured to provide field 228 when light source 208 (e.g., the therapeutic laser system) is positioned to deliver light 224 to target 206. For example, field generator 212 may be configured to apply field 228 to biological medium 204 prior to, during, and/or subsequent to application of light 224 to biological medium 204. In some implementations, an intensity of field 228 is varied such that periods of greater intensity are applied during delivery of light 224.

Field generator 212 may include a plurality of electrodes, a magnetic coil, an electret, or a combination thereof. For example, field generator 212 may include a plurality of electrodes configured to provide the field across the plurality of electrodes, as described at least with reference to FIGS. 2, 3, 4A-4C. As another example, field generator 212 may include a magnetic coil, as described at least with reference to FIG. 5. As another example, field generator 212 may include an electret, as described at least with reference to FIG. 7.

During operation of the system of FIG. 2, therapeutic treatment is performed on biological medium 204. For example, the therapeutic treatment may include a cosmetic treatment, such as a tattoo removal treatment in which laser ablation is performed to at least partially remove tattoo pigment included in target 206.

Field generator 212 is positioned adjacent (e.g., next to) biological medium 204. For example, field generator 212 may be positioned in contact with at least a portion of biological medium 204, such as a portion at or near target 206. Light source 208 is positioned to deliver light 224 (e.g., laser light) to target 206.

Field generator 212, such as a field generation system, is activated to apply field 228 through target 206 of biological medium 204. For example, a field generator system that includes field generator 212 may be turned on and field generator may generate field 228 responsive to power supplied to field generator 212.

During application of field 228 to target 206, light source 208 generates light 224, a portion of which is provided to target 206. The portion of light 224 may cause an LIOB event at the surface of a pigment agglomeration (included in target 206). The LIOB event can lead to ablation damage to target 206 and to the formation of a particle vacuole (e.g., 100) located immediately adjacent to the pigment agglomeration on the side that is closest to light source 208.

Application of field 228 prior to and/or during delivery of light 224 to target 206 affects free electrons in at least a portion (i.e., target 206) of the biological medium 204. For example, free electrons (e.g., 232) may be moved, removed, swept, or otherwise diverted away from target 206 responsive to field 228. Due to field 228, free electrons (e.g., 232) emitted into biological medium 204 are moved away from a light path of light 224. To illustrate, free electrons (e.g., 232) emitted into the dermis of biological medium 204 during the particle LIOB event are swept away from a laser beam path (of light source 208) based on field 228. This removal of free electrons (e.g., 232) aids in impeding the initiation of dermal LIOBs without adversely affecting the laser ablation of the pigment particle. As a result, remote vacuoles and the accompanying dermal damage are significantly reduced as compared to a conventional laser treatment which does not utilize (or apply) a field to a target region of a biological medium.

In some implementations, the system optionally includes head device 236. Head device 236 may be configured to contact biological medium 204 to help position light source 208 (e.g., by stabilizing the skin, positioning and/or orienting the skin). For example, head device 236 may be positioned adjacent to or in contact with a surface of biological medium 204 that includes target 206 so that the surface is normal (e.g., perpendicular) to a longitudinal axis of light 224 applied to target 206. Head device 236 may include a vacuum head configured to apply suction to a portion of biological medium 204, as described with reference to FIGS. 4A-4C. In such implementations, head device 236 may be coupled to a suction system. Additionally, or alternatively, head device 236 may include a window 406 through which light 224 can reach target 206. The head device 236 may be coupled to or integrated with in field generator 212, light source 208, or both. For example, field generator 212 may be incorporated in a portion of head device 236 as described with reference to at least FIGS. 4A and 4B.

In some implementations, the system may include a power source (not shown), such as a voltage source. The power source may be coupled to light source 208, field generator 212, head device 236, or a combination thereof. To illustrate, power source may be configured to provide power to light source 208 for generation of light 224. Additionally, or alternatively, power source may be configured to provide power, such as high voltage and low current, to field generator 212 to enable field generator 212 to generate field 228 (e.g., an electrostatic field). To illustrate, the voltage source may be configured to provide a voltage to the field generator from +1,200 to +5,000 volts or −1,200 to −5,000 volts, as illustrative, non-limiting examples. Additionally, or alternatively, power source may provide power to head device 236 to enable operation of one or more vacuum components of head device 236.

In some implementations, field generator 212 and light source 208 are incorporated into a single device, such as a probe, as described with reference to FIGS. 6A and 6B. For example, the single device may be referred to as a "Field Enhanced Laser" or an "Electric Field Enhanced Laser" ("EFE Laser"). The Field Enhanced Laser is configured to selectively providing LIOB on an absorptive target in biological medium 204. To illustrate, the Field Enhanced Laser may include a QS-laser and field generator 212 to provide a field, such as a high voltage electrostatic field, at a treatment site (e.g., target 206), as an illustrative, non-limiting example. In other implementations, field generator 212 is configured to be removably coupled to light source 208. For example, field generator 212 may be coupled to light source 208 prior to and during delivery of light 224 during a therapeutic treatment (e.g., a cosmetic treatment). After the therapeutic treatment, field generator 212 may be decoupled from light source 208.

Thus, the system of FIG. 2 advantageously provides reduced and/or limited remote vacuole formation as compared to conventional techniques in which a pulse laser is applied without application of a field (e.g., an electrostatic field). For example, field 228 may cause diversion of free electrons (e.g., 232) from the laser path of light 224 and reduce the buildup of a critical density of free electrons in biological medium 204 that could initiate LIOBs associated with remote vacuoles (e.g., 102) and cause shielding of light 224. Accordingly, laser effectiveness against an absorptive target is greater when the field is applied as compared to conventional techniques when no field is applied. Because application of the field reduces and/or limits remote vacuole formation, laser treatments over the same treatment area may be performed in quick succession and effectively to whitened tattoo areas, and/or without negatively impacting surrounding cellular structures. Additionally, laser fluence during a treatment session does not need to be reduced or limited, which permits a greater desired therapeutic effect to be realized during a single treatment session as compared to conventional techniques. By having a treatment session that is more effective as compared to conventional techniques, a patient has to undergo a fewer total number of treatments and thereby experiences less discomfort and a shorter treatment duration.

Figure 3:
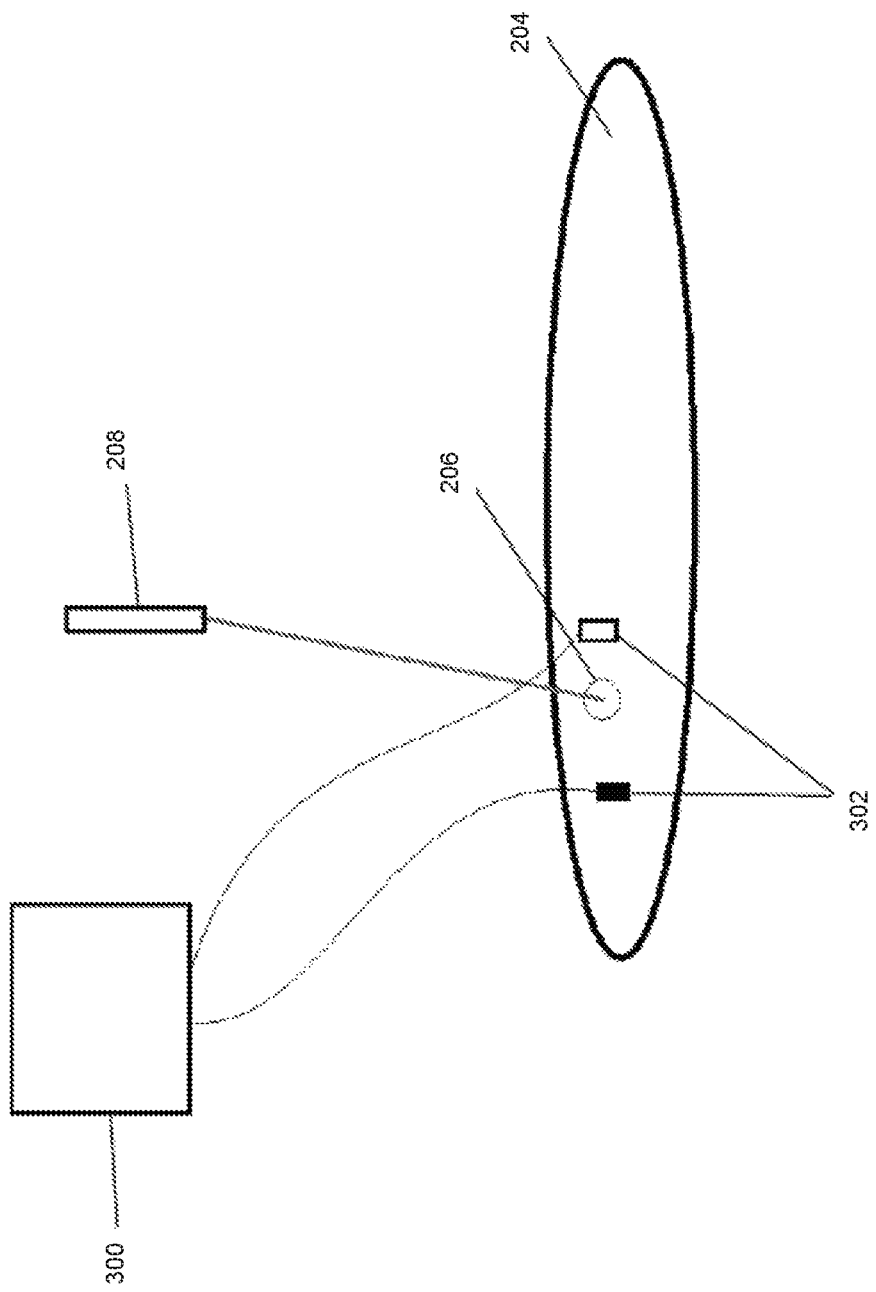
FIG. 3 depicts a block diagram of an example of an apparatus that includes a plurality of electrodes and that is configured to selectively provide LIOB to an absorptive target in a biological medium.

Referring to FIG. 3, an illustrative block diagram of an example of an apparatus for selectively providing LIOB on an absorptive target in a biological medium 204 (e.g., skin) is shown. In this example, the apparatus or system comprises a voltage source 300 and a plurality of external electrodes 302 where the electrodes that are configured to be non-conductive relative to biological medium 204 when in contact with or otherwise physically coupled to the biological medium. For example, at least a portion (e.g., up to all) of the electrode can be covered with an electrical insulator such as a polymer. In some embodiments, voltage source 300 provides a voltage potential (e.g., with low current to keep the power requirements relatively low). Voltage source 300 may provide a voltage across electrodes 302 of equal to any one, or between any two, of: −/+10 V (volts), 50 V, 100 V, 200 V, 250 V, 500 V, 750 V, 1000 V, 2000 V, 3000 V, 4000 V, 5000 V, 6000 V, 7000 V, 8000 V, 9000 V, or 10000 V. In a particular implementation, voltage source 300 may be configured to provide a voltage to the field generator from +1,200 to +5,000 volts or −1,200 to −5,000 volts, as illustrative, non-limiting examples. In another particular implementation, voltage source 300 may be configured to provide a voltage to the field generator from 500 to 500,000 volts or −500 to −500,000 volts.

In some implementations, an electric potential is applied across electrodes 302 and at least a portion of the "positive" electrode is in contact with the biological medium 204 which results in a relative negative electric field created between the electrodes. In instances where a pulsed laser (e.g., 208) is used on an absorptive target 206 in biological medium 204, this polar field causes the free electrons emitted into biological medium 204 from the absorptive target LIOB event to be removed from the pulse path of pulsed laser source 208 by repulsion from the negative electrode. This removal of free electrons from the laser path reduces the buildup of a critical density of free electrons in biological medium 204 that could initiate LIOBs. Because the laser interaction with absorptive target 206 is the source of a large quantity of free electrons, sufficient density exists to allow LIOB events at the absorptive target 206 surface, even with electric field sweeping.

In other implementations, an electric potential is applied across electrodes 302 and at least a portion of the "negative" electrode is in contact with the biological medium 204 which results in a relative positive electric field created between the electrodes. In instances in which a pulsed laser source 208 (e.g., a laser) is used on an absorptive target 206 in biological medium 204, this polar field can cause the free electrons emitted into biological medium 204 from the absorptive target LIOB event to be concentrated and energized in the laser pulse path by attraction toward the positive electrode. This concentration of energized free electrons in the laser path can aid in building a critical density of free electrons in biological medium 204. As a result, LIOBs can be produced in biological medium 204 without using high laser fluence.

Figure 4B:
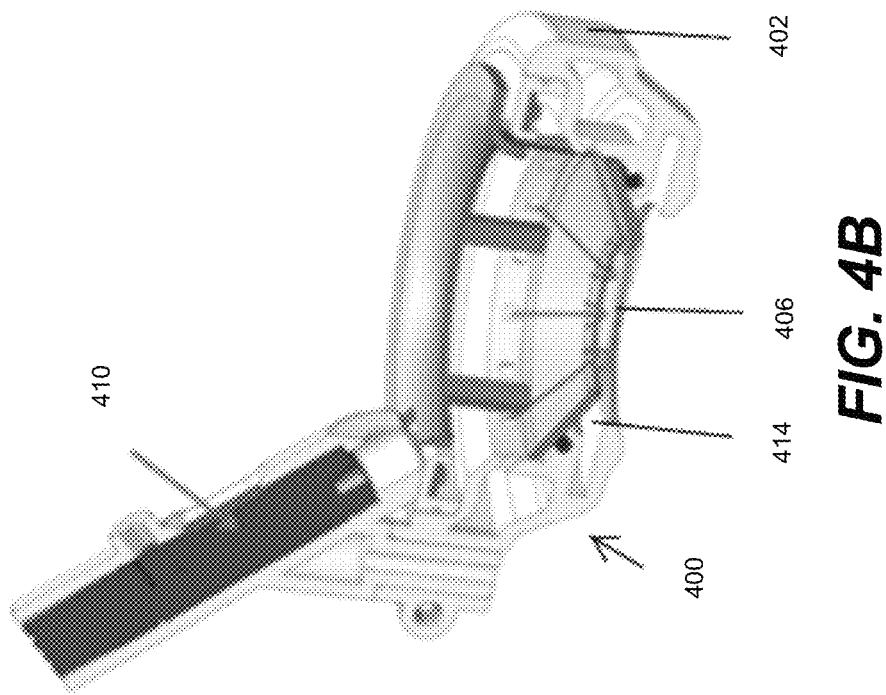
FIGS. 4A and 4B depict an exploded isometric view and an isometric view (respectively) of a first example of a vacuum head of an apparatus for selectively providing LIOB to an absorptive target in a biological medium.
Figure 4A:
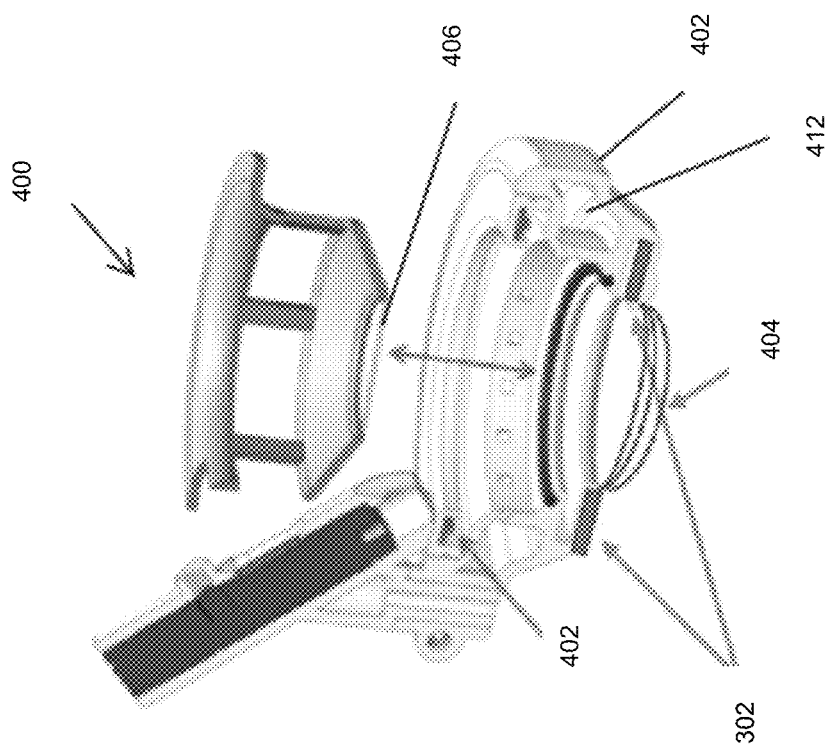

FIGS. 4A and 4B depict cross-sectional perspective views of examples of the present devices for providing selective laser induced optical breakdown in a conductive biological medium (e.g., 204). In this embodiment, the apparatus comprises a vacuum head 400 configured to assist in selectively providing LIOB to an absorptive target in a biological medium. The vacuum head 400 may include or correspond to head device 236 of FIG. 2.

As shown, vacuum head 400 is configured to be used with the components depicted in FIGS. 2-3, some of which are disposed within the vacuum head. For example, referring to FIG. 4A, vacuum head 400 includes a housing 402, as shown, that holds electrodes 302 which are, in use, electrically connected to voltage source 300. A distal (or lower in the orientation of FIGS. 4A-4B) end of vacuum head 400 is configured to be pressed against biological medium 204 (e.g., skin) such that electrodes 302 are near, but not in electrical contact with, an external surface of biological medium 204. For example, the housing of vacuum head 400 can comprise a polymer or other material that is not electrically conductive, within which at least the "sink" electrode is disposed. In such embodiments, the sink electrode(s) can be covered by the non-conductive material or simply spaced inward from a surface of the housing that is configured to contact the skin in use, while the reference electrode(s) can be disposed on or aligned with the contacting surface such that the reference electrode(s) will contact the skin in use.

As described above, voltage source 300 may provide a negative potential across electrodes 302. In some embodiments, vacuum head 400 pulls the biological medium 204 (e.g., the skin of a patient) into the vacuum head 400 such that an electric field 404 (e.g., 228) generated by the plurality of electrodes 302 is perpendicular to the axis of the laser beam. As shown, the housing of vacuum head 400 defines one or more internal channels 412 and one or more openings (e.g., an annular opening 414) through which vacuum is communicated (e.g., continuously or at multiple points around a perimeter of a treatment area) to apply suction to the skin or other biological medium. As used in this disclosure, the term "vacuum" refers to a pressure that is lower than ambient atmospheric pressure, rather than a complete absence of matter.

In the examples shown in FIGS. 4A and 4B, vacuum head 400 also comprises a window 406 (e.g., a transparent window) that allows transmission of laser pulses through the vacuum head between electrodes 302, assists with cooling of the skin or other biological medium (e.g., by providing a heat sink that draws thermal energy from the skin), and/or assists with stabilization of the skin or other biological medium (e.g., by creating an enclosed space in which the vacuum or suction can be applied to the skin). In some embodiments, window 406 can comprise a sapphire material that may, for example, be cooled prior to being placed in contact with the biological medium (e.g., skin). In some implementations, window 406 may include an electret configured to generate a field (e.g., 228).

In the examples shown in FIGS. 4A and 4B, vacuum head 400 also comprises a thermometer 410 (e.g., an infrared or other non-contact thermometer) coupled to the housing and oriented to monitor the temperature of the skin or other biological medium, and a light source (not shown) (e.g., light-emitting diode (LED) or other light source) coupled to the housing and oriented to illuminate and thereby assist with viewing the target treatment area. Other embodiments may omit window 406 in favor of an uncovered void or opening, omit thermometer 410, and/or omit the light source (e.g., LED).

Figure 4C:
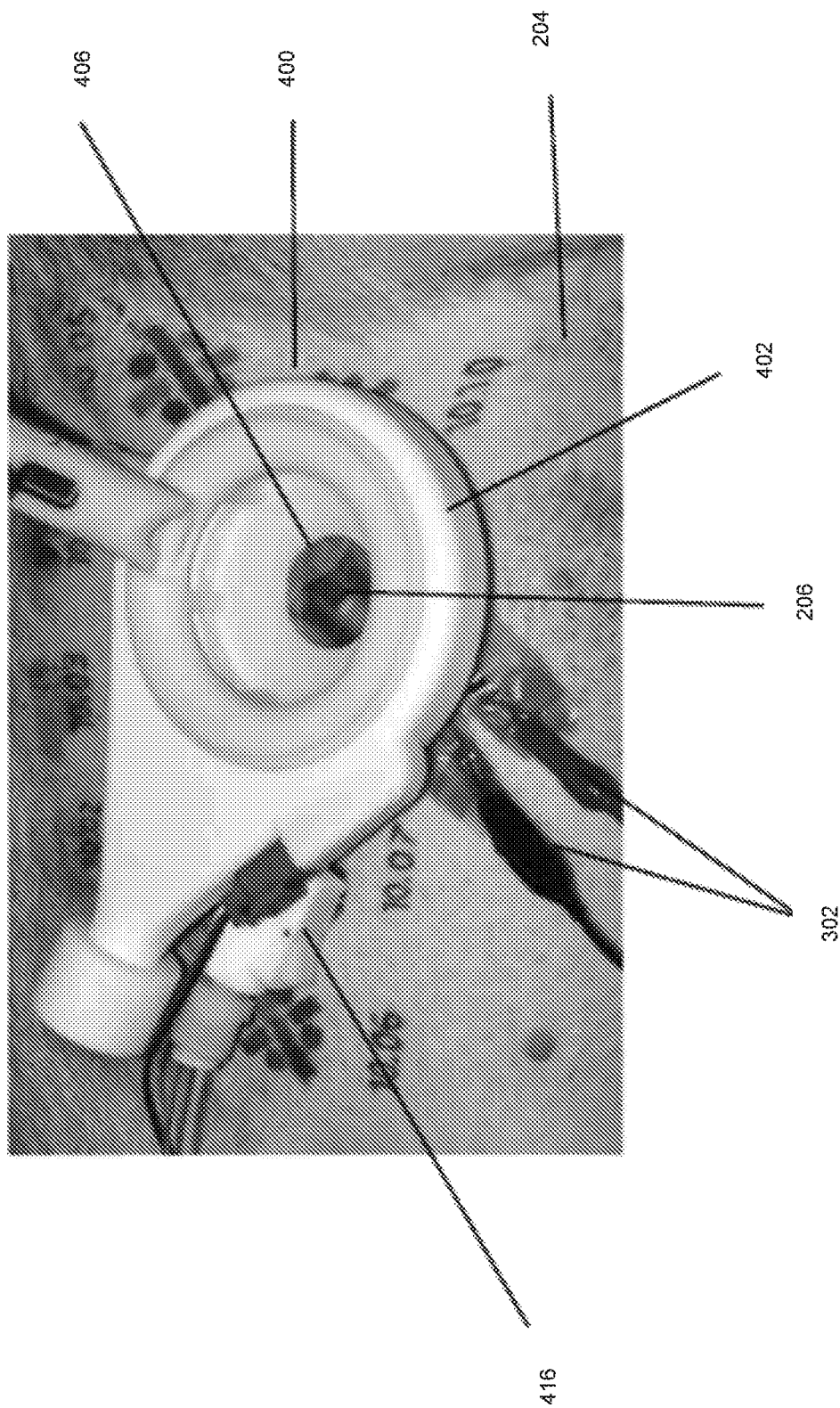
FIG. 4C is a photograph of a second example of a vacuum head of an apparatus for selectively providing LIOB to an absorptive target in a biological medium.

FIG. 4C depicts a photograph of another example of the present vacuum heads. In the example depicted in FIG. 4C, electrodes 202 are positioned between biological medium 204 and vacuum head 400. As shown, vacuum head 400 of FIG. 4C assists in isolating a section of biological medium 204 by pulling a portion of biological medium 204 to come into contact with window 406. This stabilizes the portion of biological medium 204 and allows for the electric field generated by electrodes 302 to be perpendicular to the axis of the laser beam being used to treat the absorptive target 206 in biological medium 204. As shown in FIG. 3C, the housing of vacuum head 400 includes an external connection 416 through which a vacuum source can be connected to internal channels 412 to be communicated to a treatment area.

Figure 5:
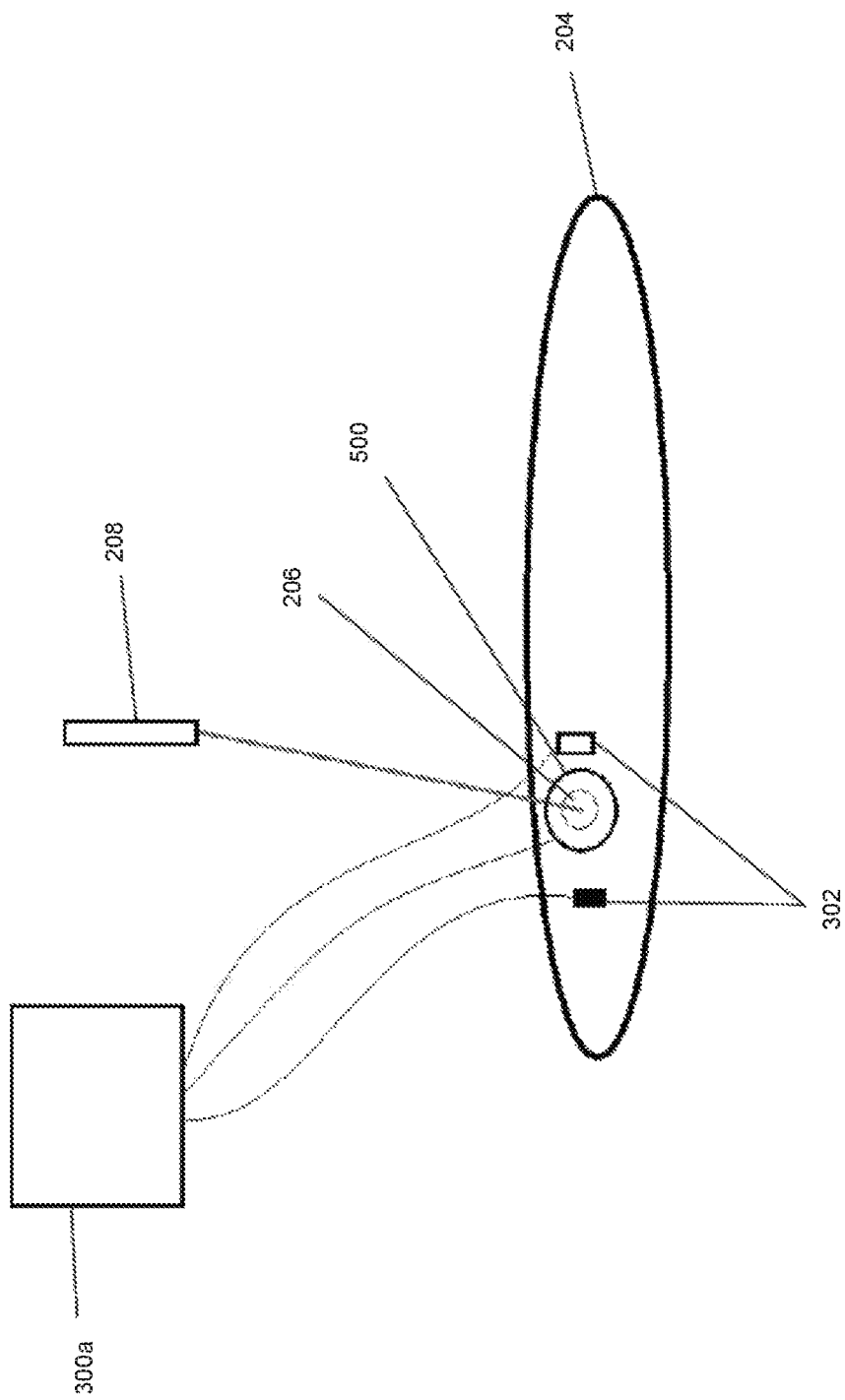
FIG. 5 depicts a block diagram of an example of an apparatus that includes a magnetic coil and that is configured to selectively provide LIOB to an absorptive target in a biological medium.

FIG. 5 depicts another embodiment of a device for selectively providing LIOB to an absorptive target 206 in a biological medium 204. The device of FIG. 5 includes a voltage source 300a, at least two external insulated electrodes 302, and a magnetic coil 500. As described above for voltage source 300, voltage source 300a can, in use, provide a negative potential across electrodes 302. In the example shown in FIG. 5, voltage source 300a is similar to voltage source 300 but is configured to also provide power to magnetic coil 500 to induce a magnetic field. The negative electric potential applied across electrodes 302 and magnetic coil 500 creates both a negative electric field and a magnetic field. These fields cause the free electrons emitted into biological medium 204 from the absorptive target LIOB event to be removed from the laser pulse path. In some embodiments, the removal of free electrons from the laser path reduces the formation of LIOBs in the biological medium 204 without completely eliminating the desired LIOB event at the site of the absorptive target 206. In other implementations, electrodes 302 may be omitted.

Figure 6A:
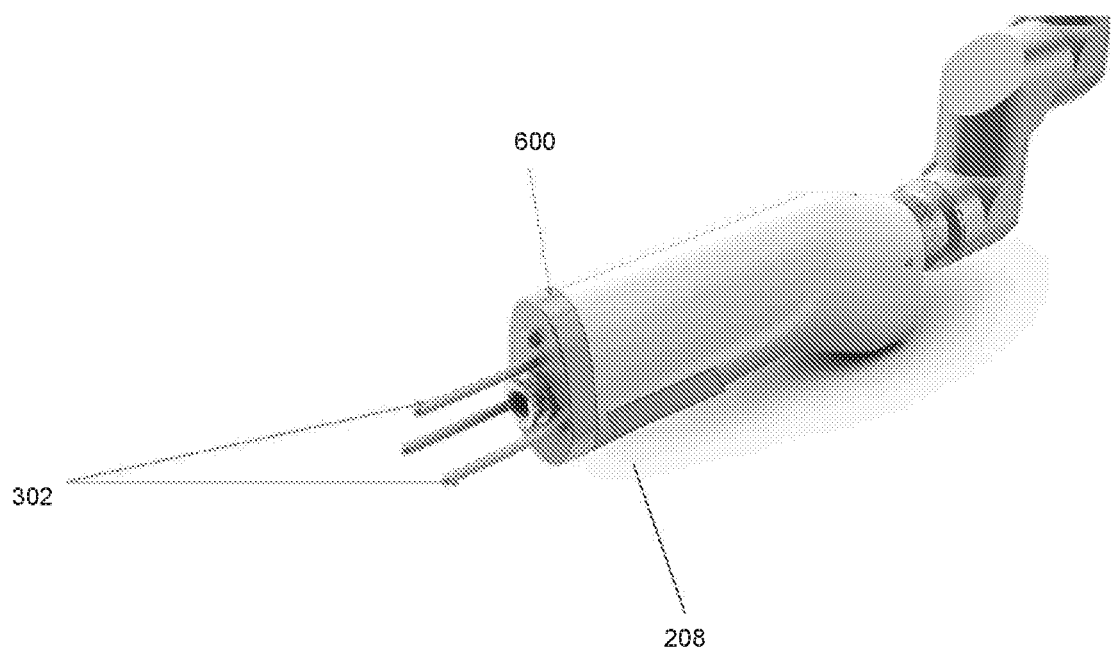
FIG. 6A depicts an isometric view of a first example of an apparatus that includes a plurality of electrodes and a laser tip and that is configured to selectively provide LIOB to an absorptive target in a biological medium.
Figure 6B:
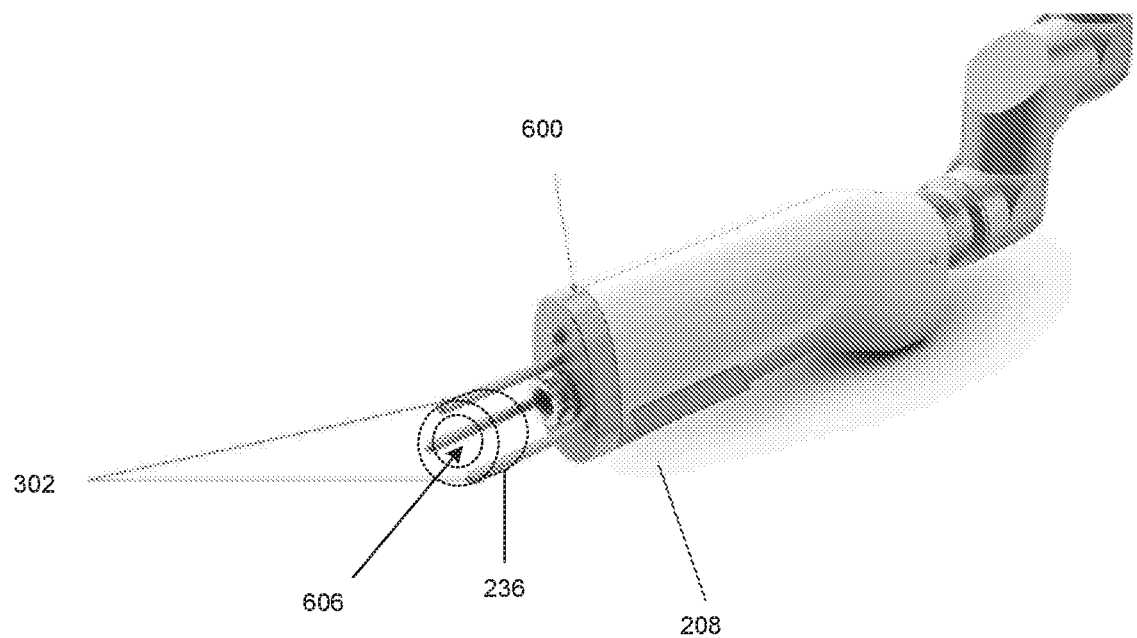
FIG. 6B depicts an isometric view of a second example of an apparatus that includes a plurality of electrodes and a laser tip and that is configured to selectively provide LIOB to an absorptive target in a biological medium.

Referring to FIGS. 6A and 6B, examples of a pulsed laser source 208 that can be included in or used with the present systems and devices are shown. For example, the pulse laser source 208 of FIGS. 6A and 6B may be used to selectively provide LIOB to an absorptive target (e.g., 206) in a biological medium (e.g., 204). In some embodiments, electrodes 302 are coupled to and extend from laser head 600 such that when the laser light is applied to skin (e.g., biological medium 204), the electrodes can be placed in contact with the skin at points around the point at which the laser is delivered to the skin. As described above, voltage source 300 (or 300a) provides a potential across the electrodes of equal to any one, or between any two, of: −/+10 V (volts), 50 V, 100 V, 200 V, 250 V, 500 V, 750 V, 1000 V, 2000 V, 3000 V, 4000 V, 5000 V, 6000 V, 7000 V, 8000 V, 9000 V, or 10000 V. When laser head 600 is aligned to deliver laser light to the skin prior to actually providing laser pulses, an electric field is first established via electrodes 302. In some embodiments, electrodes 302 establish a negative electric field causing the removal of free electrons from the laser path thereby minimizing the formation of LIOBs in biological medium 204 without completely eliminating the LIOB event at the site of the absorptive target 206.

Referring to FIG. 6B, head device 236 (depicted with dashed lines) is coupled to an end of pulsed laser source 208. Head device 236 may include or correspond to vacuum head 400 as described with reference to FIGS. 4A-4C. For example, head device 236 may include a window 606 (e.g., 406) via which a laser pulse (e.g., 224) from pulsed laser source 208 may travel.

During operation of the device of FIG. 6A or 6B, laser head 600 (containing at least two non-conductive electrodes (e.g., 302) is placed against an external surface of the biological non-transparent medium (e.g., 204). For example, laser head 600 may be placed against the external surface such that the electrodes 302 are in contact with the external surface. After placement of laser head 600, a negative electrical potential is applied across the electrodes from a voltage source, such as voltage source 300 (or 300a), and a pulsed laser beam is caused to propagate in the space between the electrodes. To illustrate, the pulsed laser beam, such as light 224 from light source 208, is provided to target 206 while a field generated by electrodes 302 is applied to target 206 (e.g., biological medium 204).

FIG. 7 depicts another example of a device to be used in conjunction with a light source 208 (e.g., a therapeutic laser) for selectively providing LIOB to an absorptive target 206 in a biological medium 204 comprising at least one electret 700 configured to provide an electric field to the site to be treated with a laser. In some implementations, electret 700 is transparent and allows for the transmission of laser pulses through the electret 700 itself. Electret 700 can comprise any material that holds an electric field including various forms of silicon dioxide (e.g., quartz, etc.) or various synthetic polymers (e.g., fluoropolymers, polypropylene, polyethylene terephthalate, etc.).

Figure 8:
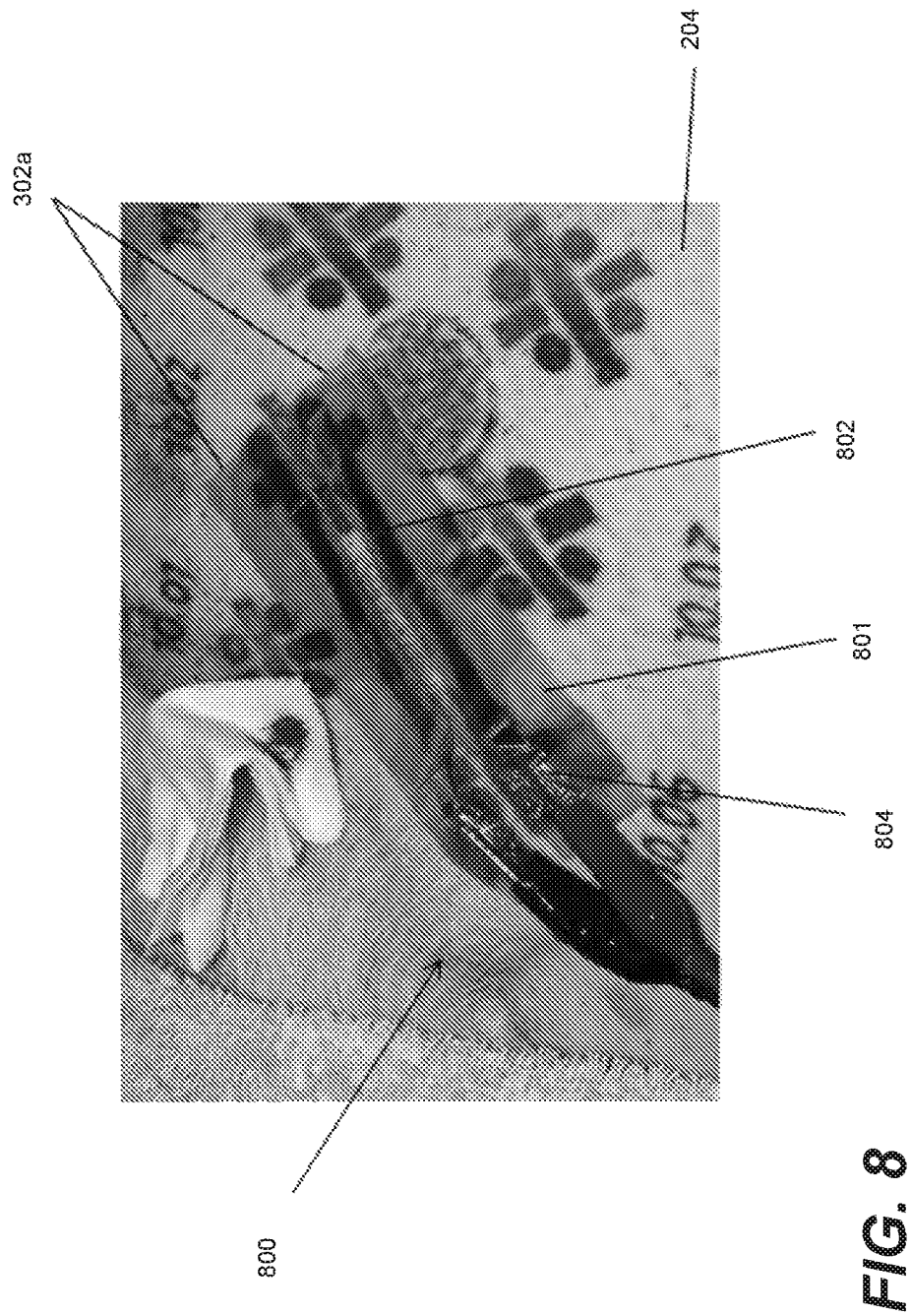
FIG. 8 is a photograph of an example of an apparatus that includes a plurality of insulated electrodes and that is configured to selectively provide LIOB to an absorptive target in a biological medium.

FIG. 8 depicts an example 800 of external insulated electrodes 302a. In this embodiment, insulated electrodes 302a each comprise an outer insulation layer 801, an inner conductive layer 802, and a connection point 804 at which the electrodes are connected to a voltage source. As described above, the one of the electrodes 302a that is used or intended to be used as a "sink" electrode may be entirely covered with the non-conductive layer, whereas the other of the electrodes intended to be used as the "reference" electrode will have at least a portion of an electrically conductive surface exposed to contact a patient's skin during use. In some embodiments, inner conductive layer 802 comprises a conductive foil made from a conductive material such as, for example: copper, silver, gold, aluminum, iron, steel, brass, bronze, alloys, and/or the like. Outer insulation layer 801 can comprise an electrically insulating film constructed from an insulating plastic. As shown, inner conductive layer 802 can be sandwiched between two outer insulation layers 801 one or both of which has an adhesive surface configured to be attached to biological medium 204. In the embodiment shown, inner conductive layer 802 has dimensions of ¼ inches×0.0025 inches, is constructed of copper foil, and is sandwiched between two strips of 0.001 inch thick Kapton® tape.

Figure 9:
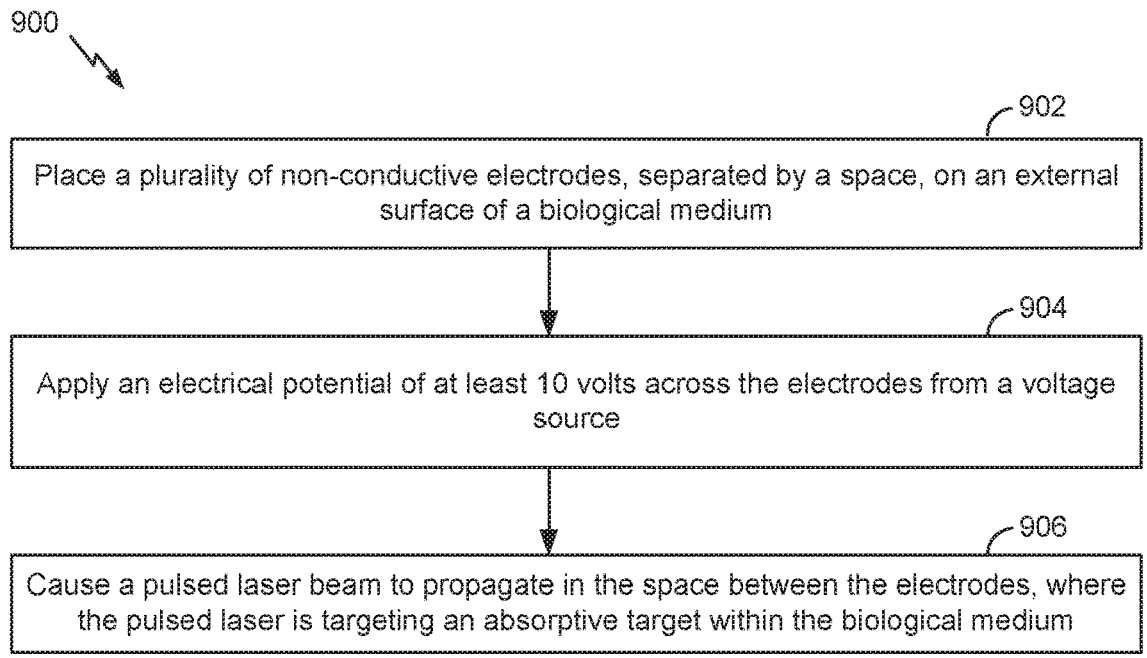
FIG. 9 is a flowchart of an illustrative example of a method for selectively providing LIOB to an absorptive target in a biological medium.
Figure 10:
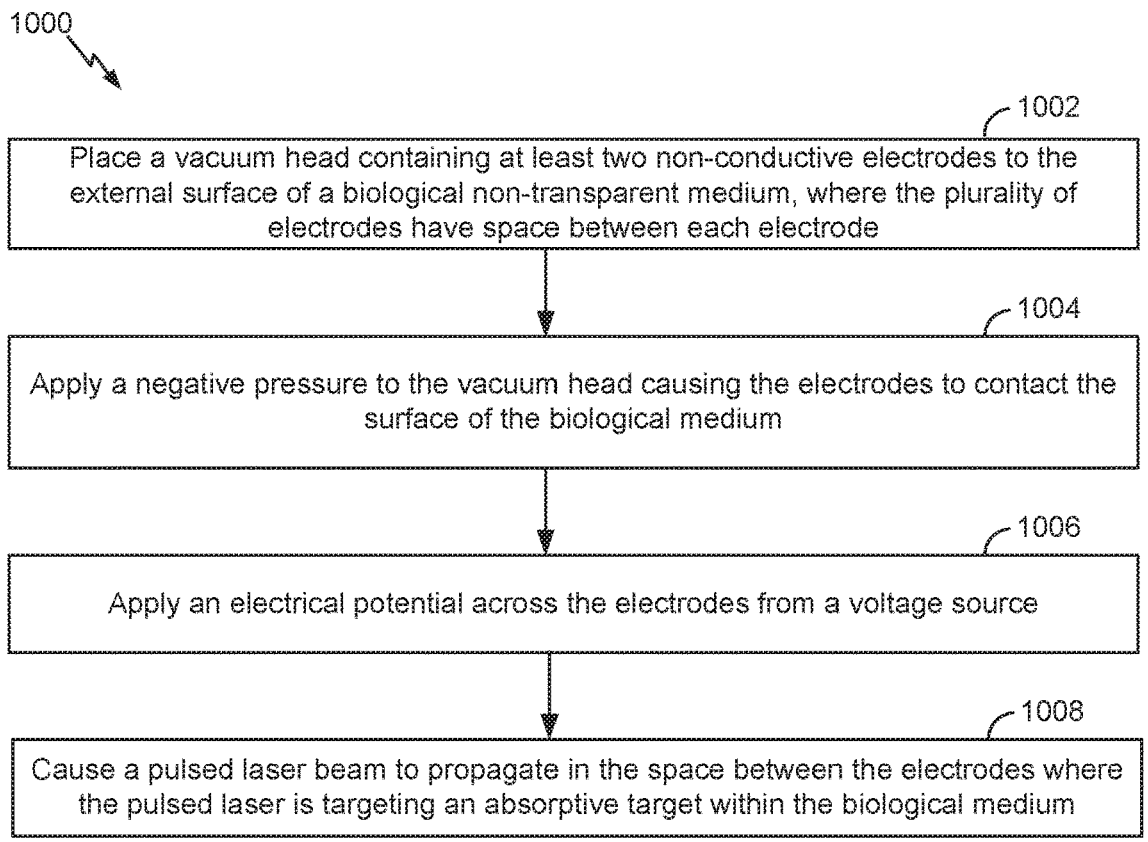
FIG. 10 is a flowchart of an illustrative example of a method for using a vacuum head for selectively providing LIOB to an absorptive target in a biological medium.

Referring to FIGS. 9 and 10, methods of selectively providing LIOB to an absorptive target 206 in a biological medium 204 are shown. For example, the methods of FIGS. 9-10 may be implemented by the apparatus and/or systems described herein with reference to FIGS. 2, 3, 4A-4C, 5, 6A-6B, and 7.

Referring to FIG. 9, method 900 includes placing a plurality of electrodes separated by a space, on the external surface of a biological medium 204, at 902. The biological medium may include or correspond to biological medium 204 as described herein at least with reference to FIG. 3. The plurality of electrodes may include or correspond to field generator 212, electrodes 302 (or 302a), Method 900 also includes applying an electrical potential of at least 10 volts to the electrodes from the voltage source, at 904. For example, the voltage source may include or correspond to voltage source 300 (or 300a).

Method 900 further includes causing a pulsed laser beam to propagate in the space between electrodes where the pulsed laser is targeting an absorptive target within the biological medium, at 906. For example, the pulsed laser beam may include or correspond to light 224 generated by light source 208 (e.g., pulsed laser). The absorptive target within the biological medium may include or correspond to target 206 within biological medium 204.

In some implementations of method 900, a negative electric potential is applied across electrodes thereby creating a negative electric field. In such implementations, the negative electric field causes the free electrons emitted into the medium from the absorptive target LIOB even to be removed from the laser pulse path. Accordingly, method 900 of FIG. 9 enables the removal of free electrons from the laser path and inhibits the formation of LIOBs in the biological medium without completely eliminating the LIOB event at the site of absorptive target. In some embodiments, the electric potential applied across the electrodes is equal to any one, or between any two, of: −/+10 V (volts), 50 V, 100 V, 200 V, 250 V, 500 V, 750 V, 1000 V, 2000 V, 3000 V, 4000 V, 5000 V, 6000 V, 7000 V, 8000 V, 9000 V, or 10000 V.

Referring to FIG. 10, method 1000 includes placing a vacuum head containing at least two non-conductive electrodes to the external surface of the biological non-transparent medium, where the plurality of electrodes have space between each electrode, at 1002. For example, the vacuum head may include or correspond to head device 236 or vacuum head 400. The biological medium may include or correspond to biological medium 204 as described herein at least with reference to FIG. 2. The plurality of electrodes may include or correspond to field generator 212, electrodes 302 (or 302a), Method 1000 also includes applying a negative pressure to the vacuum head causing the electrodes to contact the surface of the biological medium, at 1004, and applying an electrical potential across the electrodes from a voltage source, at 1006. For example, the voltage source may include or correspond to voltage source 300 (or 300a).

Method 1000 further includes causing a pulsed laser beam to propagate in the space between the electrodes where the pulsed laser is targeting an absorptive target within the biological medium, at 1006. For example, the pulsed laser beam may include or correspond to light 224 generated by light source 208 (e.g., pulsed laser). The absorptive target within the biological medium may include or correspond to target 206 within biological medium 204.

First Experimental Results

Experiments were conducted on Gottingen minipigs to observe the effects of selective LIOB in laser skin treatments using some embodiments of the present disclosure. A study was undertaken to demonstrate the reduction of "whitening" caused by intradermal vacuoles as a result of laser treatment while generating an electric field in the treated tissue.

Two pigs were tattooed with patterns containing black pigment. These tattoos were left to mature for over four months. Six tattoo sites were treated with either laser only ("Laser Only"), laser under a positive electric field ("Laser+EF(+)") or laser under a negative electric field ("Laser+EF(−)"). Additionally, one non-tattooed skin site was treated with the laser as a control ("Negative Control"). For the initial study, each site tested was placed under a negative pressure utilizing a device similar to those shown in FIGS. 4A-4C. As shown in FIG. 4C, insulated electrodes 302 where placed on the underside of the sapphire window 406 of this negative pressure device. All laser treatments were performed through this sapphire window 406. The laser settings used in the study were as follows: Medlite IVTM 1064 nM Q-switched Nd:YAG, 3.5 J/cm$^2$, 1 Hz, 4 mm spot size. The electric field was created by an electrostatic voltage source that was able to produce high voltage with little current. The voltage source was set at 0 volts, plus (+)1200 volts, or minus (−)1200 volts relative to the pig for Laser Only, Laser+EF(+) or Laser+EF(−), respectively.

Prior to the laser treatment, colorimetric readings were taken at each tattoo site. Immediately after treatment, another set of colorimetric readings were taken. For each tattoo site, each pre-treatment colorimetric reading was normalized to the post-treatment colorimetric reading to provide an indication of dermal vacuole formation. A higher normalized post-treatment colorimetric reading indicates greater dermal vacuole formation. Additionally, biopsies of each treatment site were taken within 1 minute of the laser treatment ("Day 0") and 48 hours post laser treatment ("Day 2") for histological evaluation.

Figure 11:
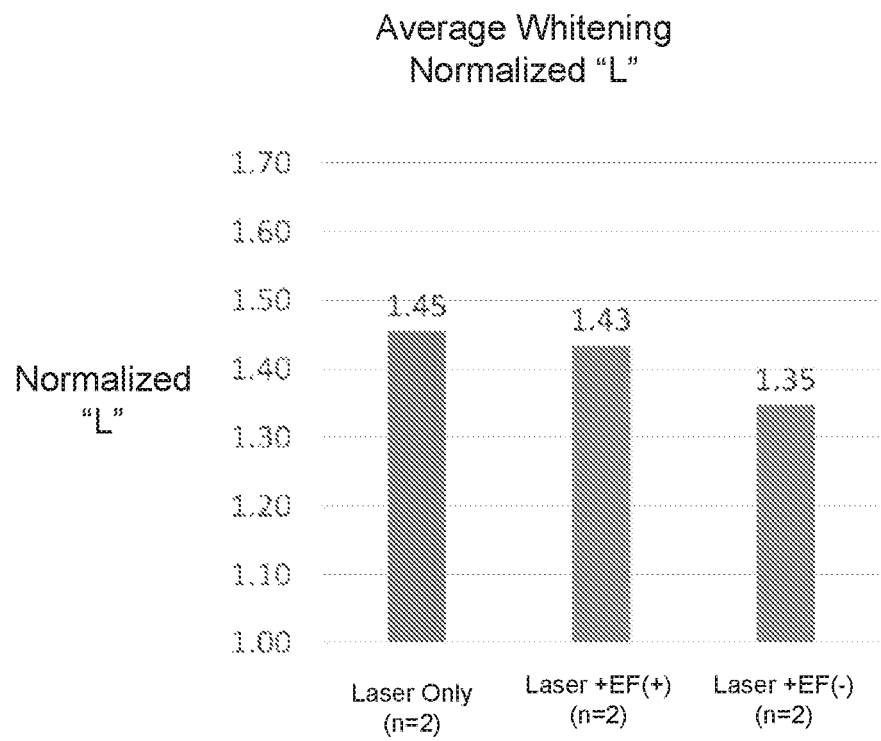
FIG. 11 is a graph that depicts experimental data regarding using electric fields in laser-based therapies.

Referring to FIG. 11, a bar graph illustrating the results of a colorimetric study on the effect of electric fields on dermal vacuole formation is shown. The Laser+EF(−) had a lower normalized colorimetric reading than Laser Only or Laser+EF(+). The normalized colorimetric reading for the Laser+EF(+) was comparable to Laser Only. Lower normalized colorimetric readings indicate that the Laser+EF(−) resulted in a lower level of vacuole formation during laser treatment of a tattoo site.

Figure 12:
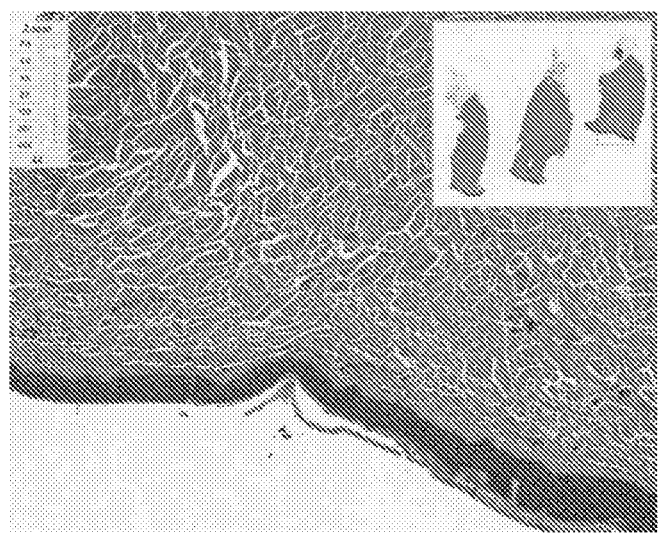
FIG. 12 depicts a histological image of laser treated non-tattooed dermis demonstrating no vacuole formation.

Referring to FIG. 12, a histological image of non-tattooed dermis treated with a pulsed laser, which served as a negative control in the performed experiments, is shown. As shown by FIG. 12, no particle vacuoles or remote vacuoles are present. This demonstrates that at the laser fluences used in the study, the presence of tattoo pigment agglomerations is required to generate vacuoles.

FIGS. 13A and 13B depict Day 0 histological images of two tattoo sites treated with Laser Only. Each show that particle vacuoles 100 and remote vacuoles 102 are both present. Particle vacuoles 100 tend to be small in size and are typically located on the surface of pigment agglomerations that face the epidermis. This occurs where the surface of the pigment agglomeration is ablated by the laser resulting in the formation of the vacuole on the surface-side of the agglomeration being exposed to the laser. The remote vacuoles 102 are smaller and relatively spherical in shape when compared to the particle vacuoles 100.

Figure 14B:
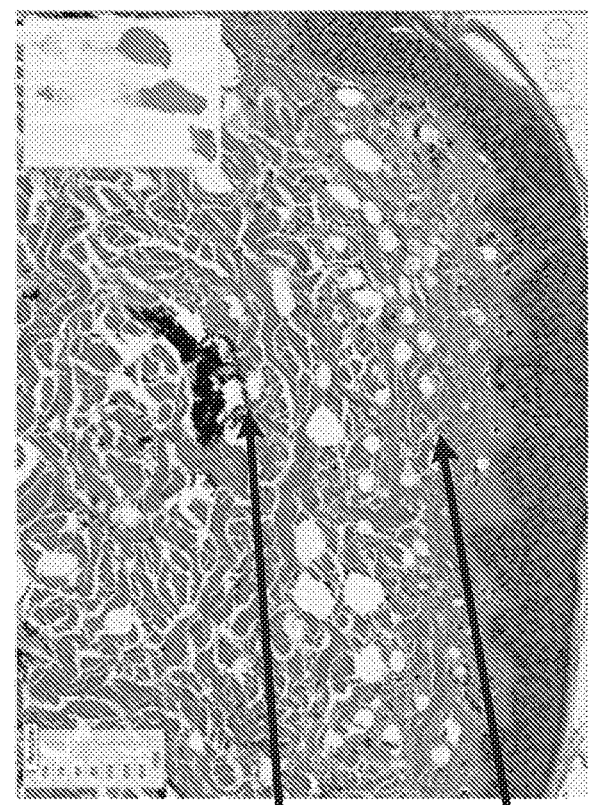
FIGS. 14A and 14B depict histological images of "Laser+EF(+)" treated tattooed dermis.
Figure 14A:
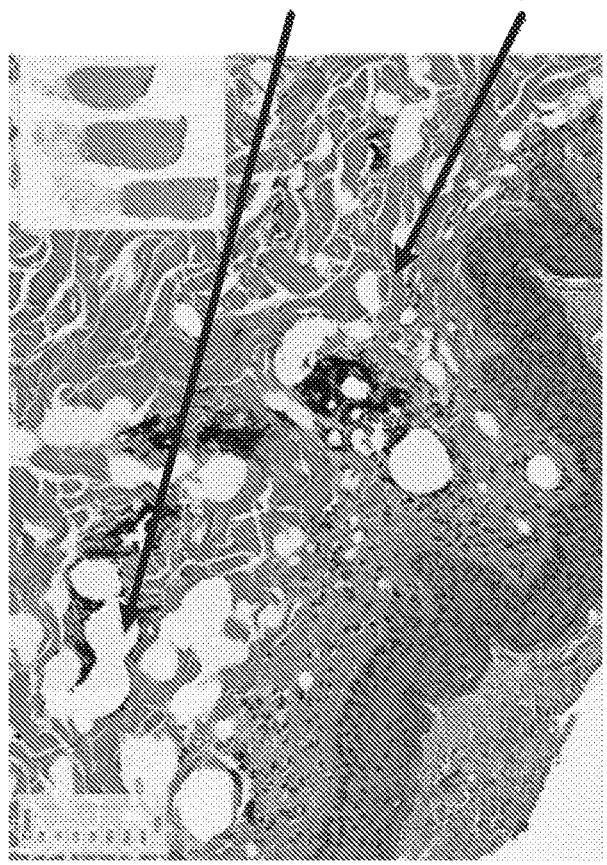

FIGS. 14A and 14B depict Day 0 histological images of two tattoo sites treated with Laser+EF(+). Each show that particle vacuoles 100 and remote vacuoles 102 are both present. Similar to the images depicted in FIGS. 13A and 13B, particle vacuoles 100 tend to be small in size and are typically located on the surface of pigment agglomerations that face the epidermis. However, remote vacuoles 102 are seen in large numbers in both FIGS. 14A and 14B. Here, the positive electric field excites free electrons at the site resulting in the buildup of a high density of free electrons. The exited free electrons make the dermal environment more susceptible to LIOB events which result in remote vacuole 102 formation.

FIGS. 15A and 15B depict Day 0 histological images of two tattoo sites treated with Laser+EF(−). Just like with FIGS. 13A, 13B, 14A, and 14B, particle vacuoles 100 are present. Unlike FIGS. 13A, 13B, 14A, and 14B, however, remote vacuoles 102 are only minimally present. Additionally, in comparison to the findings in Laser Only and Laser+EF(+), the particle vacuoles 100 are larger in size and encompass the entirety—and not just the upper surface—of the pigment agglomeration. The negative electric field pushes free electrons away from the site, thereby reducing the buildup of a critical density of free electrons within the dermis which can result in an LIOB event. As a result, the formation of remote vacuoles 102 is minimized. Additionally, the pushing of free electrons away from the site aids in delaying the initiation of LIOB event on the surface of the pigment agglomeration. This then allows the laser pulse to absorb longer into the pigment agglomeration before the plasma event shields the pigment agglomeration from the laser. This leads to the greater ablation of the pigment agglomeration and the production of a large particle vacuole 100. Greater ablation of the pigment agglomeration by Laser+EF(−) means that tattoos can be eliminated faster.

FIGS. 16A and 16B depict Day 2 histological images of two tattoo sites treated with Laser+EF(−) and show that pigment particles 1600 that have been treated with a Laser+EF(−) are transported away from the tattoo site more quickly than Laser Only. FIGS. 16A and 16B show pigment particles 1600 located deep in the dermis 48 hours post laser treatment. In comparison, images of Laser Only treated tattoo sites rarely demonstrate pigment particles 1600 located deep in the dermis 48 hours post laser treatment.

Based on the difference in results from the laser treatment of non-tattooed skin (Negative Control) and laser treatment of the tattoo sites, the formation of both particle vacuoles 100 and remote vacuoles 102 are a direct result of the action of the pulsed laser on the tattoo pigment agglomerations 104. When the pulsed laser is absorbed into the pigment agglomeration 104, a plasma plume quickly forms. This plume causes the water surrounding the pigment agglomeration 104 to undergo a phase change resulting in a particle vacuole 100 (via steam production). Additionally, the plasma plume violently emits free electrons, ions and nano-size pigment particles 1600 from the surface of the pigment agglomeration 104 (e.g., a surface of a pigment particle included in the pigment agglomeration 104) into the dermis. It is believed that these violently emitted free electrons result in formation of a critical density of free electrons in the dermis. These free electrons are then able to absorb laser photons leading to an LIOB event and remote vacuole 102 formation.

Comparing the histology of the Laser+EF(+) site (FIGS. 14A and 14B) to Laser Only (FIGS. 13A and 13B) site (i.e., laser to tattoo site without an electric field), both studies have formed an abundance of particle vacuoles 100 and remote vacuoles 102. Surprisingly, it appears that the number of remote vacuoles 102 in the Laser+EF(+) treatment site were substantially greater than that of the Laser Only treatment. It is thought that the presence of a positive electric field increased the free electron excitation in the biological medium near the negative electrode leading to a selective increase in LIOB formation in the biological medium 204.

On the other hand, comparing the histology of the Laser+EF(−) site (FIGS. 15A and 15B) to Laser Only site (FIGS. 13A and 13B), both studies have formed an abundance of particle vacuoles 100. However, surprisingly, the size of the particle vacuoles 100 associated with the negative electric field were much larger than the particle vacuoles 100 associated with Laser Only treatments. Again, as discussed above, it is believed that the negative electric field pushes free electrons away from the treatment site near the negative electrode. This results in a delay of the initiation of LIOB event on the surface of the pigment agglomeration 104 resulting in the laser pulse having a longer time to be absorbed by the pigment agglomeration 104. This leads to greater ablation of the particle agglomeration 104 as evidenced by the large particle vacuoles 100.

Laser+EF(−) only results in a minimal number of remote vacuoles 102 being generated. The free electrons emitted from the LIOB of the pigment agglomeration 104, were quickly dispersed from the laser path in the dermis before a critical electron density could form. This in turn inhibited the formation of LIOB in the medium resulting in the selective suppression of the formation of remote vacuoles 102.

Laser treatment of pigment agglomerations 104 while within an electric field, results in greater transport of the pigment particles 1600 into the deep dermis. Ablating pigment agglomerations 104 while within an electric field results in the generation of electrostatically charged pigment particles. These charged and/or smaller particles are then more easily carried away from the tattoo site which further aids in the fading of treated tattoo sites.

Second Experimental Results

A second study was conducted to evaluate the relationships between: 1) Laser induced dermal vacuole formation (i.e., whitening) and dermal injury, and 2) laser induced dermal vacuole formation and tattoo fading. The secondary objective was to evaluate the EFE Laser treatments compared to standard 1064 Q-switched Nd:YAG laser (Q-switched laser) tattoo removal treatments for dermal vacuole formation, dermal injury and tattoo fading. The dermal vacuole formation and dermal injury were assessed histologically. Accelerated tattoo fading was assessed colorimetrically The EFE Laser was evaluated at a CRO animal facility (MPI, Kalamazoo, Mich.). A tattooed porcine animal model, approved by the Animal Care Committee, was used in this study. Gottingen Mini-pigs (~30 kg) were tattooed by a professional tattoo artist on both lateral sides, under general anesthesia, with multiple circular (1 cm diameter) black tattoo spots (See, e.g., FIG. 4C) and allowed to mature for at least 3 months prior to the initiation of the study.

An EFE Laser and standard Q-switched laser were evaluated in a study using Gottingen Mini-pigs (~30 kg) tattooed with multiple circular (1 cm$^2$) black tattoo spots. Tattoo sites were treated with either a single-pass laser treatment using an unmodified Q-switched laser (Laser-Only) or using a 1064 nm Q-switched laser in conjunction with an external electrostatic field (EFE Laser). Vacuole formation was assessed histologically immediately post treatment and dermal injury was assessed histologically 2 to 6 days post treatment. Fading of the treated tattoo sites was assessed by comparing colorimetric readings of the tattoos pre-treatment and at 8 weeks following treatment using a spectrophotometer (Konica Minolta CM-700d, Konica Minolta Sensing Americas, Inc., Ramsey, N.J.).

Prior to the start of treatments, the animals where placed under general anesthesia. Selected tattoo sites were then treated with either a standard short pulse laser (Laser Only) or an EFE Laser. The laser used in both Laser Only and EFE Laser studies was a 1064 nm QS Laser (MedLite IV, Continuum Biomedical, acquired by Hologic, Inc., Marlboro, Mass.) The laser parameters used for Laser Only and EFE Laser treatments during each individual study were comparable and included the following: Pulse rate of 1 Hz; laser fluences ranging from 4.0 J/cm$^2$ to 9.0 J/cm$^2$ per pass; and, laser spot sizes ranging from 3 mm to 4 mm.

Referring to FIG. 4C, for the EFE Laser, the electric field generation setup used with the laser is shown. This setup consisted of a skin vacuum head 400 having a sapphire window 406 with at least one insulated electrode 302 attached to the inner surface of the window 406. A custom DC power supply (not shown) provided high voltage (range: +/−1200 volts to +/−5000 volts) across the electrodes 302 during the laser treatment. This resulted in an electrostatic field being established at the treatment site. In some tests, when a single electrode was used on the sapphire window 406, a larger return electrode pad was used on a distant location from the treatment site. In performing the laser treatments using the electric field generation setup the laser treatment was performed within 1 cm of the active electrode.

Following the laser treatments, histological examination of biopsied tissue was performed to assess the number of vacuoles formed and the amount of dermal injury. For the assessment of vacuoles, a 3 mm punch biopsy of the tattoo treatment site was performed immediately following the Laser Only or EFE Laser treatment. Hematoxylin and eosin (H&E) stained slides were prepared from the biopsied tissue. Dermal vacuole formation for each treatment was determined by counting the number of vacuoles in a defined area of the histology image.

To assess dermal injury, a 3 mm punch biopsy of the tattoo treatment site was performed 2-6 days following Laser Only or EFE Laser treatment. Herovici stained slides were prepared from the biopsied tissue. Dermal injury for each treatment was determined using a 5-point dermal injury scale by assessing damage to the epidermis and dermis. The 5-point scale ranged from no injury to significant epidermis and dermal collagen injury as denoted by substantial Herovici staining. ('0'=No injury; '1'=Minimal collagen injury; '2'=Mild collagen injury; '3'=Localized loss of epidermis plus minimal collagen injury; '4'=No loss of epidermis, but major collagen injury; and, '5'=Lost of epidermis plus major collagen injury).

Fading of the treated tattoo sites was assessed using a handheld spectrophotometry (Konica Minolta CM-700d, Konica Minolta Sensing Americas, Inc., Ramsey, N.J.) configured to record the L*a*b* color space values. Tattoo fading was calculated by percentage change of the colorimetric difference (distance in color space) metric $\Delta E^*$, where $\Delta E^* = ((\Delta L^*)^2 + (\Delta a^*)^2 + (\Delta b^*)^2)^{1/2}$. The colorimetric distance metric $\Delta E^*$ for tattoo readings taken at 8 weeks was compared to the pre-treatment colorimetric $\Delta E^*$ value to calculate the percentage tattoo fading.

Figure 17:
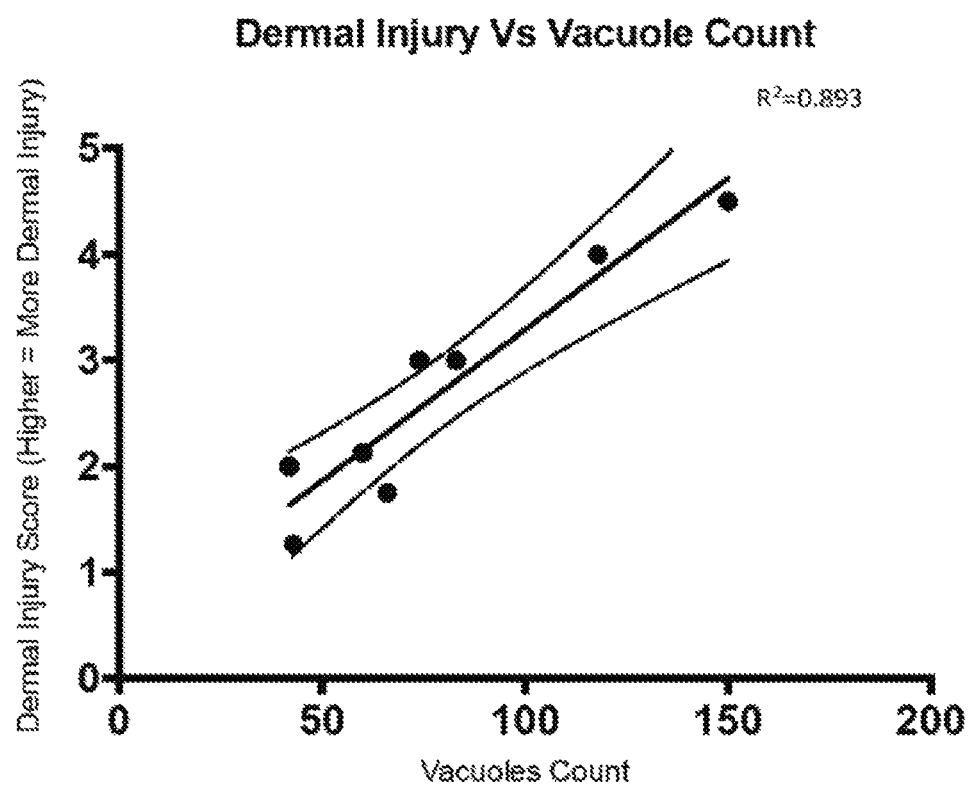
FIG. 17 is a graph that depicts experimental data regarding the relationship between laser induced dermal vacuole formation and dermal injury.

Referring to FIG. 17, the relationship between laser induced dermal vacuole formation and dermal injury was investigated. In four separate laser treatments over a 3 month period, the mean dermal vacuole counts (N=8) was compared to the mean of the dermal injury score (N=8) from the Laser Only treatments and EFE Laser treatments. The results of this investigation are shown in FIG. 16 and demonstrate a very strong positive correlation (r=0.945, R$^2$=0.893) between the mean dermal vacuole count immediately post laser treatment and the dermal injury score 2-6 days post laser treatment.

Figure 18B:
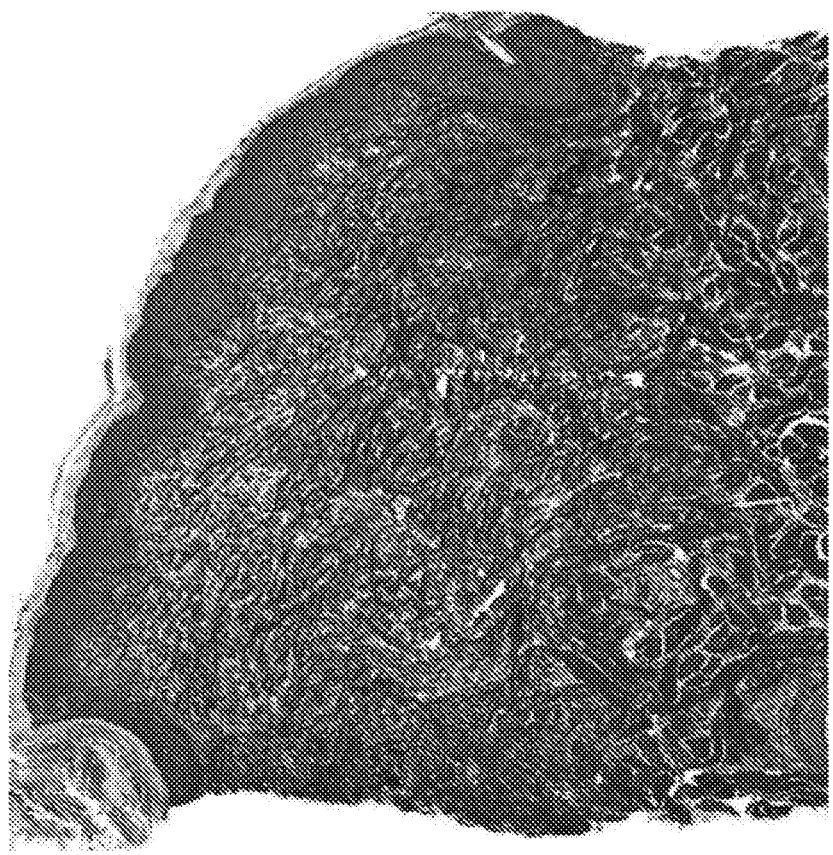
FIGS. 18A and 18B depict histological images showing dermal vacuole formation and dermal injury for Laser Only treated tattoo sites.
Figure 18A:
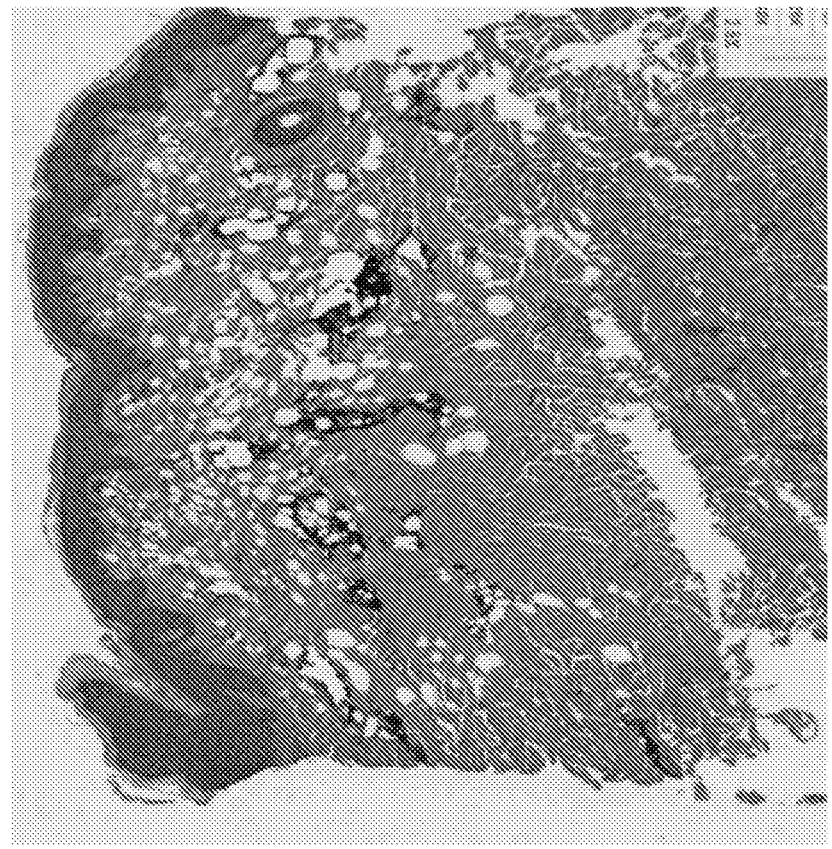

Referring to FIGS. 18A-18B and FIGS. 19A-19B, examples of histological images showing dermal vacuole formation and dermal injury for Laser Only and EFE Laser treated tattoo sites are shown, respectively. FIG. 18A is the histological image (H&E stained) of the tattoo site on porcine skin immediately post-Laser Only treatment showing a significant number (>100) of dermal vacuoles (white voids) consisting of a small number of irregular shaped larger particle vacuoles and a large number of smaller spherical remote vacuoles (small circular voids in the dermis remote to the pigment particles). FIG. 18B is a Herovici stained image of the same treatment site 4 days post-Laser Only treatment, showing significant dermal injury and new collagen (Type III) formation. Collagen stains light blue with the Herovici stain, compared to the old collagen (Type I) that stains dark blue/purple.

Figure 19A:
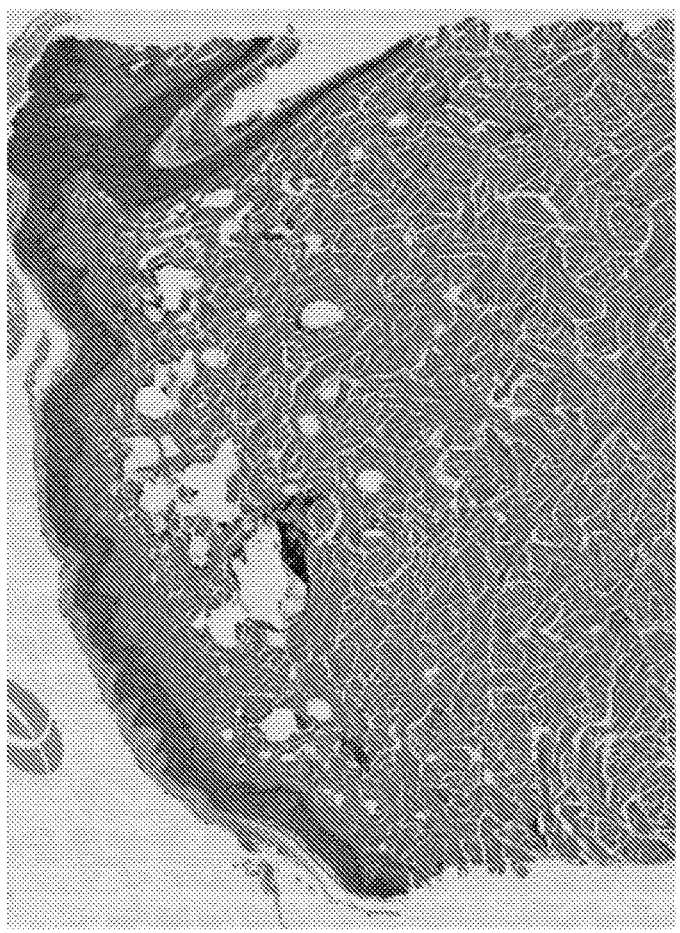
FIGS. 19A and 19B depict histological images showing dermal vacuole formation and dermal injury for EFE Laser treated tattoo sites.
Figure 19B:
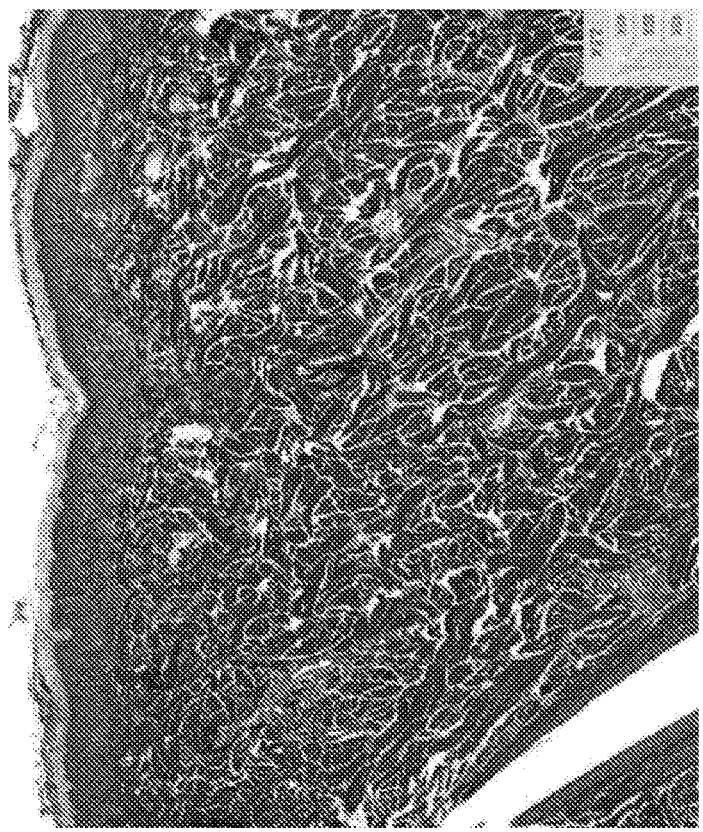

In contrast, as shown in FIG. 19A, the histological image (H&E stained) of the tattoo site on porcine skin immediately post-EFE Laser had a smaller number of dermal vacuoles (~33). While the number of particle vacuoles (large, irregular shaped white voids adjacent to pigment particles) was comparable to tattoo sites with Laser Only treatment (~10-20), the number of remote vacuoles present was less. Likewise, FIG. 19B provides a histological image (Herovici stained), of the same treatment site 4 days post-EFE Laser treatment, demonstrating minimal dermal injury (minimal light blue staining) and new collagen formation.

Figure 20:
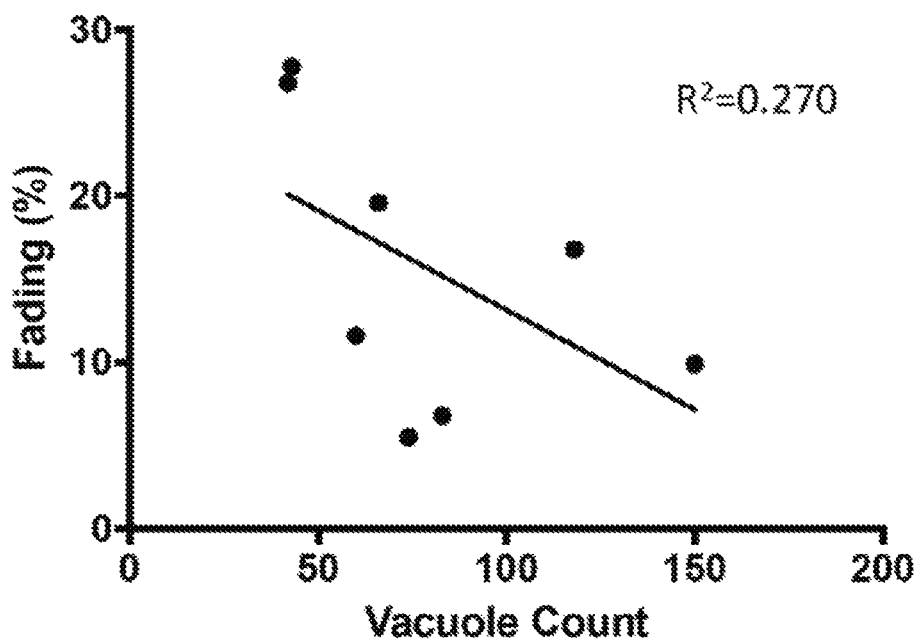
FIG. 20 is a graph that depicts experimental data regarding the relationship between laser induced dermal vacuole formation and tattoo fading.

Referring to FIG. 20, the relationship between laser induced dermal vacuole formation and tattoo fading at 8 weeks was evaluated. The mean dermal vacuole counts (n=8) were compared to the mean of percentage change in $\Delta E^*$ (n=8) from the EFE Laser treatments and Laser Only treatments. As shown in FIG. 20, the results demonstrate a moderate negative correlation (r=−0.52) between vacuole formation and tattoo fading (i.e., more dermal vacuoles result in less tattoo fading.)

Figure 21:
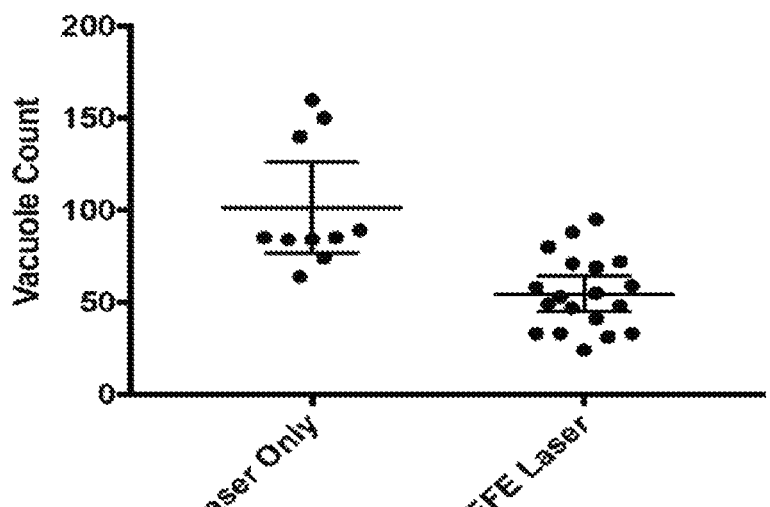
FIG. 21 is a scatter plot that depicts experimental data regarding the dermal vacuole count following treatment with EFE Laser and Laser Only

The secondary objective of this study was to evaluate the EFE Laser treatments, in comparison to standard laser tattoo removal treatments, for dermal vacuole formation, dermal injury and tattoo fading. Referring to FIG. 21, the scatter diagram (with a horizontal line for mean and error bars for 95% CI) shows the dermal vacuole count following treatment with EFE Laser and Laser Only. EFE Laser treatments showed a significantly lower mean dermal vacuole count after a single laser pass in comparison to the Laser Only treatments. The mean vacuole count for EFE Laser was 55 (n=19). The mean vacuole count for Laser Only was 101 (n=10). In a t-test (2-tailed, non-paired, homoscedastic), the difference between the two groups was statistically significant ($P<0.0001$).

Figure 22:
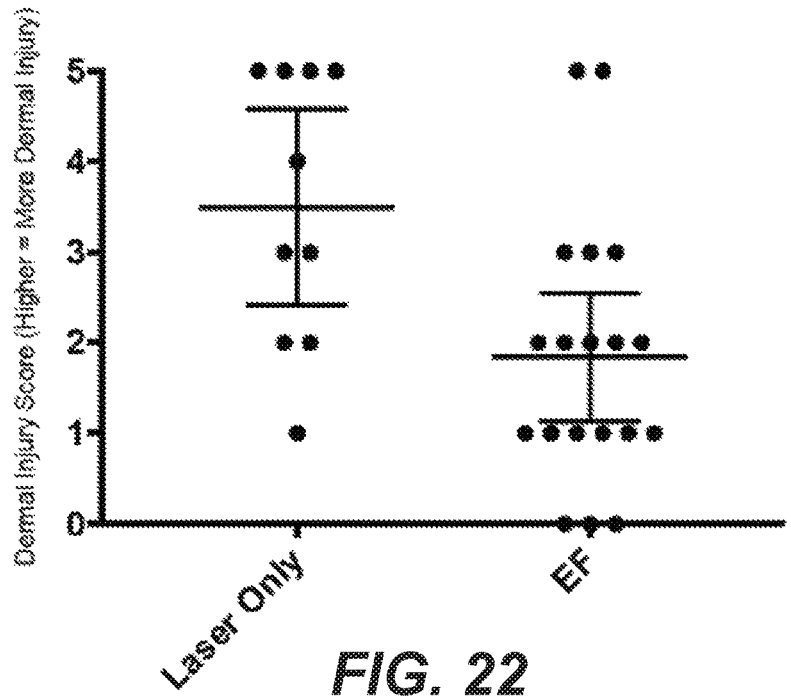
FIG. 22 is a scatter plot that depicts experimental data regarding the dermal injury score following treatment with EFE Laser and Laser Only.

Referring to FIG. 22, the scatter diagram (with lines for mean and error bars for 95% CI) shows the dermal injury score following treatment with EFE Laser and Laser Only. EFE Laser treated sites showed a smaller mean dermal injury score in comparison to Laser Only treated sites. The mean dermal injury score for EFE Laser was 1.84 out of 5 (n=19). The mean dermal injury score for Laser Only was 3.5 out of 5 (n=10). In a t-test (2-tailed, non-paired, homoscedastic), the difference between the two groups was statistically significant ($P<0.01$).

Figure 23A:
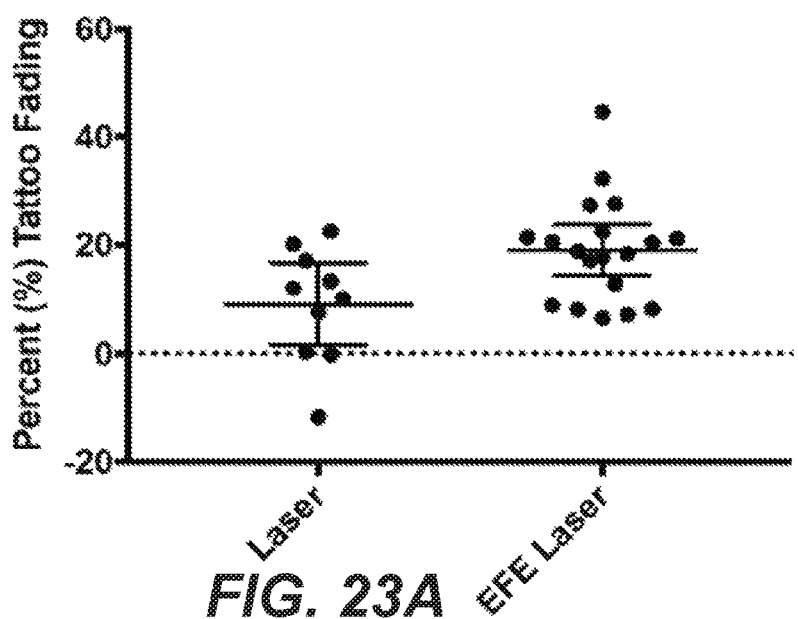
FIG. 23A is a graph that depicts experimental data regarding percentage of tattoo fading at 8 weeks between EFE Laser and Laser Only treated tattoo sites.
Figure 23C:
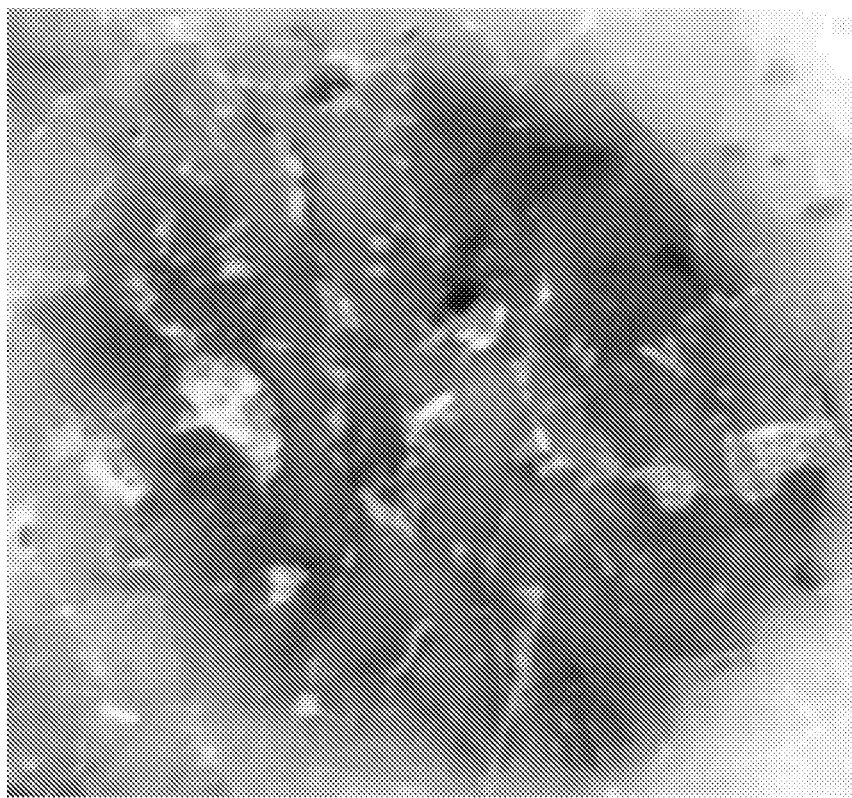
FIGS. 23B and 23C are photographs of an example of the results for representative tattoo sites treated with the EFE Laser and treated with Laser Only.
Figure 23B:
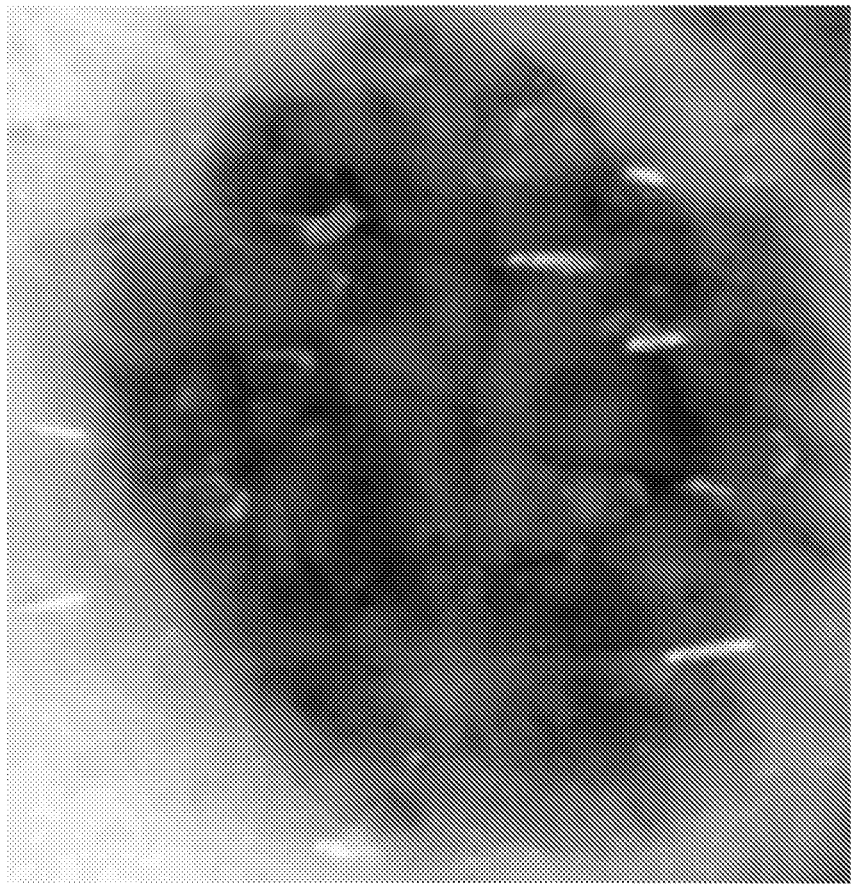

Referring to FIG. 23A, a comparison of the percentage of tattoo fading at 8 weeks between EFE Laser (n=19) and Laser Only (n=10) treated tattoo sites is shown. The scatter diagram (with a horizontal line for mean and error bars for 95% CI) demonstrates accelerated tattoo fading after a single laser pass using EFE Laser compared to the Laser Only. The mean fading for EFE Laser is 19.1%. The mean fading for Laser Only is 9.2% ($P<0.05$). Finally, FIGS. 23B and 23C provide photographic images showing improved fading for a representative tattoo site treated with the EFE Laser in comparison to Laser Only. For example, FIG. 23B shows fading with Laser Only (4 $J/cm^2$ @ 4 mm; 1 Hz) and FIG. 23C shows fading with EFE Laser (5000 Kv; 4 $J/cm^2$ @ 4 mm; 1 Hz).

This study demonstrated that greater laser induced dermal vacuole formation increases dermal injury and decreases tattoo fading efficacy. The EFE Laser was able to minimize the amount of laser induced dermal vacuole formation during laser treatment of tattoo sites resulting in reduced dermal injury and improved tattoo fading. It is believed that lower vacuole formation results in a reduction of laser shielding and light scattering allowing more laser energy to reach the tattoo ink particle.

This study provided evidence that the EFE Laser in the treatment of the tattoo sites results in the formation of fewer dermal vacuoles, less dermal injury and improved tattoo fading when compared to standard laser treatments. In addition to improving laser based tattoo treatments, the use of an electric field can mitigate free electrons from thermionic emissions during laser ablation treatments (hair removal, vein removal, etc.) to provide safer, more effective treatments.

The above description and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this disclosure. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, connections may be substituted, or both. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments. Accordingly, no single implementation described herein should be construed as limiting and implementations of the disclosure may be suitably combined without departing from the teachings of the disclosure.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. An apparatus for providing tissue therapy, the apparatus comprising:
a direct current (DC) voltage source; and
a field generator having a plurality of electrodes configured to provide an electrical field across the plurality of electrodes; and
a laser light source configured to deliver laser light along a laser light path to a portion of a biological medium during application of the electrical field;
wherein the DC voltage source is electrically connected to the electrodes;
wherein a first one of the electrodes comprises an electrically conductive surface configured to contact the biological medium, and a second one of the electrodes is configured to not conduct current to the biological medium;

wherein the field generator is configured to apply the electrical field to the portion of the biological medium such that free electrons are diverted away from the portion of the biological medium along the laser light path; and wherein the biological medium comprises skin or tissue.

2. The apparatus of claim 1, further comprising:

a vacuum head configured to be connected to a vacuum source;

wherein a portion of the plurality of electrodes are contained within the vacuum head;

wherein the vacuum head is configured to apply suction to the portion of the biological medium; and wherein the vacuum head is configured to permit light to reach the portion of the biological medium when suction is applied.

3. The apparatus of claim 2, wherein the vacuum head comprises a window through which the laser light can reach the portion of the biological medium.

4. The apparatus of claim 3, wherein:

the laser light source includes a therapeutic laser system configured to deliver the laser light through the window to the portion of the biological medium;

the laser light has an axis; and the electrical field applied to the portion of the biological medium, when suction is applied to the portion of the biological medium by the vacuum head, is perpendicular to the axis of the laser light.

5. The apparatus of claim 1, further comprising:

a magnetic coil;

wherein the DC voltage source is further configured to provide DC power to the magnetic coil; and wherein the magnetic coil, when so powered, is configured to induce a magnetic field in the portion of the biological medium.

6. A method comprising:

actuating, based on direct current (DC) power, the apparatus for providing tissue therapy of claim 1 to apply the electrical field from the field generator through the portion of the biological medium; and delivering the laser light from the laser light source to the portion of the biological medium such that free electrons are diverted away from the portion of the biological medium along the laser light path.

* * * * *